(12) United States Patent
Li et al.

(10) Patent No.: US 12,030,939 B2
(45) Date of Patent: Jul. 9, 2024

(54) BISPECIFIC ANTIBODY BINDING BCMA AND CD3

(71) Applicant: SHANDONG NEW TIME PHARMACEUTICAL CO., LTD., Shandong (CN)

(72) Inventors: Qiang Li, Shanghai (CN); Shixiang Jia, Shanghai (CN); Lili Zhao, Linyi (CN); Guimin Zhang, Linyi (CN); Zhong Liu, Linyi (CN); Xinlu Ma, Shanghai (CN); Yuan Yan, Shanghai (CN); Zhenyu Li, Linyi (CN); Xingxia Hu, Linyi (CN); Yuhua Zhang, Shanghai (CN); Bin Li, Linyi (CN)

(73) Assignee: Shandong New Time Pharmaceutical Co., Ltd., Shandong (CN)

( * ) Notice: Subject to any disclaimer, the term of this patent is extended or adjusted under 35 U.S.C. 154(b) by 0 days.

(21) Appl. No.: 17/290,401

(22) PCT Filed: Sep. 26, 2019

(86) PCT No.: PCT/CN2019/108057
§ 371 (c)(1),
(2) Date: Apr. 30, 2021

(87) PCT Pub. No.: WO2020/088164
PCT Pub. Date: May 7, 2020

(65) Prior Publication Data
US 2023/0416385 A1    Dec. 28, 2023

(30) Foreign Application Priority Data
Nov. 1, 2018  (CN) .......................... 201811294887.4

(51) Int. Cl.
C07K 16/30   (2006.01)
A61K 39/395  (2006.01)
(Continued)

(52) U.S. Cl.
CPC ...... *C07K 16/2809* (2013.01); *A61K 39/3955* (2013.01); *A61K 45/06* (2013.01);
(Continued)

(58) Field of Classification Search
None
See application file for complete search history.

(56) References Cited

U.S. PATENT DOCUMENTS 9,441,034 B2 *  9/2016  Sivakumar .............. A61P 35/00
2009/0252683 A1  10/2009  Kischel et al.
(Continued)

FOREIGN PATENT DOCUMENTS

CN   105358570 A    2/2016
CN   106279418 A    1/2017
(Continued)

OTHER PUBLICATIONS

Ahamadi-Fesharaki et al., Single-Chain Variable Fragment-Based Bispecific Antibodies: Hitting Two Targets with One Sophisticated Arrow. Mol Ther Oncolytics. Mar. 23, 2019;14:38-56.
(Continued)

*Primary Examiner* — Claire Kaufman
(74) *Attorney, Agent, or Firm* — McCarter & English, LLP; Maria Laccotripe Zacharakis; Yu Lu

(57) ABSTRACT

The invention provided herein relates to methods and uses of a bispecific antibody, which specifically binds the surface antigen CD3 of immune cells and the BCMA antigen on the surface of tumor cells and which may bind to human CD3 with high affinity, induce T cell proliferation, and mediate tumor cell killing effects. The bispecific antibody may be used to mediate the T cell-specific killing of target cells in in vitro tests.

15 Claims, 6 Drawing Sheets

Specification includes a Sequence Listing.

(51) Int. Cl.
    A61K 45/06    (2006.01)
    A61P 35/00    (2006.01)
    C07K 16/28    (2006.01)
    C07K 16/32    (2006.01)
    C07K 16/46    (2006.01)
    C12N 15/62    (2006.01)
    C12N 15/85    (2006.01)
    A61K 39/00    (2006.01)

(52) U.S. Cl.
    CPC .......... *A61P 35/00* (2018.01); *C07K 16/2803* (2013.01); *C07K 16/2863* (2013.01); *C07K 16/2878* (2013.01); *C07K 16/2887* (2013.01); *C07K 16/3007* (2013.01); *C07K 16/303* (2013.01); *C07K 16/32* (2013.01); *C07K 16/468* (2013.01); *C12N 15/62* (2013.01); *C12N 15/85* (2013.01); *A61K 2039/505* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/524* (2013.01); *C07K 2317/526* (2013.01); *C07K 2317/53* (2013.01); *C07K 2317/565* (2013.01); *C07K 2317/622* (2013.01); *C07K 2317/626* (2013.01); *C07K 2317/73* (2013.01); *C07K 2317/92* (2013.01); *C07K 2317/94* (2013.01)

(56) References Cited

U.S. PATENT DOCUMENTS

| | | |
|---|---|---|
| 2017/0218077 A1 | 8/2017 | Raum et al. |
| 2017/0327579 A1 | 11/2017 | Vu et al. |
| 2019/0184026 A1 | 6/2019 | Li et al. |
| 2020/0157185 A1 | 5/2020 | Gao et al. |

FOREIGN PATENT DOCUMENTS

| | | | |
|---|---|---|---|
| CN | 106317226 A * | 1/2017 | ............. A61K 38/36 |
| CN | 107286248 A | 10/2017 | |
| WO | 2011/050262 A2 | 4/2011 | |
| WO | 2012/066058 A1 | 5/2012 | |
| WO | 2013/072406 A1 | 5/2013 | |
| WO | 2014/140248 A1 | 9/2014 | |
| WO | 2015/052536 A1 | 4/2015 | |
| WO | 2017/072716 A1 | 5/2017 | |
| WO | 2017/134134 A1 | 8/2017 | |
| WO | 2017/223111 A1 | 12/2017 | |
| WO | 2018/175279 A2 | 9/2018 | |

OTHER PUBLICATIONS

Asano et al., Cytotoxic enhancement of a bispecific diabody by format conversion to tandem single-chain variable fragment (taFv): the case of the hEx3 diabody. J Biol Chem. Jan. 21, 2011;286(3):1812-8.

Hipp et al., A novel BCMA/CD3 bispecific T-cell engager for the treatment of multiple myeloma induces selective lysis in vitro and in vivo. Leukemia. Aug. 2017;31(8):1743-1751.

Wu et al., T cell engaging bispecific antibody (T-BsAb): From technology to therapeutics. Pharmacol Ther. Feb. 2018;182:161-175.

Yao, W., Introduction to Biotechnological Pharmacy, 3rd Edition. China Medical Science Press. Bispecific Antibody, pp. 238-239, Aug. 31, 2015.

Chinese Office Action for Application No. 201910915568.9, dated Mar. 16, 2022.

* cited by examiner

BISPECIFIC ANTIBODY BINDING BCMA AND CD3

CROSS-REFERENCE TO RELATED APPLICATIONS

This application is a U.S. national stage filing, under 35 U.S.C. § 371(c), of International Application No. PCT/CN2019/108057, filed on Sep. 26, 2019, which claims priority to Chinese Patent Application No. 201811294887.4, filed on Nov. 1, 2018, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created Jan. 18, 2024, is named 134361-00202_ST25.txt and is 22,791 bytes in size.

FIELD OF TECHNOLOGY

The present invention relates to the field of immunology, particularly to an anti-CD3 bispecific antibody which mediates the killing of T cells and to use of the antibody, particularly the use in treating cancer.

BACKGROUND

Multiple myeloma is a second most common hematological malignant tumor, the uncontrolled proliferation of monoclonal plasma cells in bone marrow leads to the overproduction of monoclonal immunoglobulin and immunosuppression, as well as osteolysis and terminal organ injury. There are currently two monoclonal antibodies have been endorsed for clinical use, and multiple myeloma treatment regimens have significantly improved the survival rate of patients over the past decade. Despite this, the existing treatment regimens still fail to meet the current treatment needs, especially for relapsed/refractory patients who are resistant to the current treatment.

B cell maturation antigen (BCMA) is a highly plasma cell specific antigen that plays an important role in regulating the maturation and differentiation of B cells into plasma cells by participating in proliferation-inducing ligand (APRI). BCMA expression is limited to B cell lineage and mainly exists on plasma cells and plasmablasts, and to a certain extent exists on memory B cells, but does not exist on peripheral and juvenile B-cells essentially, having not been expressed in other normal tissue cells. BCMA is also expressed on multiple myeloma cells and is participated in leukemia and lymphoma. Together with its family members TACI (transmembrane activator and cyclophilin receptor ligand interactor) and BAFF-R (B cell activating factor receptor), BCMA regulates different aspects of humoral immunity, B cell development, and homeostasis. The expression of BCMA appears in the later stage of B-cell differentiation and is beneficial to the long-term survival of plasmablasts and plasma cells in bone marrow. The target deletion of the BCMA gene in mice resulted in a significant reduction in the number of long-lived plasma cells in the bone marrow, indicating that BCMA is important for its survival. BCMA overexpression or stimulation of APRIL by BCMA in multiple myeloma cells directly upregulates key immune checkpoint molecules, which may contribute to immunosuppression of the bone marrow microenvironment.

T lymphocytes play an important role in the process of cellular immunity. The cellular immunity mediated by T cells specifically recognizes antigenic peptides presented by major histocompatibility complex (MHC) on the cell surface primarily through the T cell receptor (TCR). It plays an important role in eliminating diseased cells in vivo and preventing the occurrence of tumors. Because of the expression of MHC on the surface of most cancer cells is down-regulated or even deleted, enabling tumor cells to escape immune killing, thereby develop tumors.

T cell-engaging bispecific antibodies (TCBs) represents a very effective way to redirect activated cytotoxic T cells to tumors. As a part of the T cell receptor, CD3 expressed in mature T cells, can transduce the activation signal generated by TCR recognition antigen. TCBs are capable of binding to surface tumor antigen and CD3 ε subunit of T cell receptor simultaneously, providing a physical connection between T cells and tumor cells, thus effectively activating quiescent T cells to kill tumor cells, achieving the effect of treating tumors dormant (Smits N C, Sentman C L, Journal of Clinical Oncology, 2016: JC0649970). Because of T cell bispecific bypass the co-stimulation requirements of TCR antigen recognition and T cell activation, they eliminate the need for tumor-specific immunity and overcome many obstacles faced by T cells in tumor microenvironment.

In recent years, in order to solve the problem of correctly assembling two different semi-antibodies, scientists have designed and developed bispecific antibodies with a variety of structures. In general, there are two categories, one kind of bispecific antibody does not comprise Fc region, comprising BiTE, DART, TrandAbs, bi-Nanobody, etc. The advantage of this kind of structural double antibody is small molecular weight, can be expressed in prokaryotic cells without considering the problem of correct assembly; The disadvantages is that there is no antibody Fc segment, molecular weight is low, leading to a short half-life. Moreover, this form of double antibody is easy to polymerize, has poor stability and low expression, so its clinical application is limited to some extent. Another kind of bispecific antibodies retains the Fc domain, e.g., the configuration of Triomabs, kih IgG, Cross-mab, orthoFab IgG, DVD IgG, IgG scFv, scFv2-Fc, etc. This kind of double antibody forms IgG-like structure with large molecular structure, and the process of endocytosis and recirculation mediated by FcRn gives it a longer half-life; While retaining some or all effector functions mediated by Fc, such as antibody-dependent cell-mediated cytotoxicity (ADCC), complement-dependent cytotoxicity (CDC) and antibody-dependent phagocytosis (ADCP). However, this kind of double antibody can not completely eradicate the generation of mismatched products, while the residual fractions of any mismatched molecules are difficult to separate from the products, and this method requires a large EU numbering of genetic engineering modifications, such as mutations, against the two antibody sequences, which cannot achieve the purpose of simplicity and universality.

Therefore, the present invention intends to develop a BCMA bispecific molecule with improved performance in terms of product half-life, stability, safety and productivity.

SUMMARY

The purpose of the present invention is to provide a tetravalent homodimeric bispecific antibody molecule targeting immune effector cell antigen CD3 and tumor antigen BCMA. Such bispecific antibody can significantly inhibit or kill tumor cells in vivo, but its nonspecific killing effect on normal cells with low expression of BCMA is significantly reduced, meanwhile, the controllability of toxic and side effects caused by overactivation of effector cells is increased, and its physicochemical properties and in vivo stability are significantly improved.

In particularly, the first aspect of the present invention discloses a bispecific antibody, which is composed of two identical polypeptide chains bonded covalently to form a tetravalent homodimer, wherein each of the polypeptide chains sequentially comprises a first single-chain Fv specifically binding to a tumor antigen BCMA each polypeptide chain from N end to C end, a second single-chain Fv specifically binding to an effecter cell antigen CD3, and an Fc fragment; wherein the first single-chain Fv and the second single-chain Fv are connected by a linker peptide, and the second single-chain Fv and the Fc fragment are connected directly or by a linker peptide, and the Fc fragment does not have effector functions such as CDC, ADCC and ADCP.

Wherein, the first single-chain Fv comprises a VH domain and a VL domain connected by a linker peptide, and amino acid sequence of the linker peptide is (GGGGX (SEQ ID NO: 23))$_n$, wherein X is Ser or Ala, n is a natural number from 1 to 5; preferably X is Ser, preferably n is 3.

In a preferred embodiment of the present invention, an amino acid sequence of the linker peptide L1 is (GGGGS (SEQ ID NO: 22))$_3$, and in other preferred embodiments, the amino acid sequence of the linker peptide L1 further comprises (GGGGS (SEQ ID NO: 22))$_1$ or (GGGGS (SEQ ID NO: 22))$_2$ or (GGGGS (SEQ ID NO: 22))$_4$ or (GGGGS (SEQ ID NO: 22))$_5$ or (GGGGA (SEQ ID NO: 28))$_1$ or (GGGGA (SEQ ID NO: 28))$_2$ or (GGGGA (SEQ ID NO: 28))$_3$ or (GGGGA (SEQ ID NO: 28))$_4$ or (GGGGA (SEQ ID NO: 28))$_5$.

Preferably, the first single chain Fv comprises:
(1) a VH domain, comprising HCDR1, HCDR2 and HCDR3 having a sequence as shown in SEQ ID NO: 1, 2 and 3 respectively, or comprising HCDR1, HCDR2 and HCDR3 having a sequence at least 80%, 85%, 90%, 92%, 95%, 97%, 98%, 99% or higher identity to SEQ ID NO: 1, 2 and 3 respectively, or comprising HCDR1, HCDR2 and HCDR3 having a sequence as shown in SEQ ID NO: 1, 2 and 3 respectively except for one or more amino acid substitutions (for example conservative substitutions); and
(2) a VL domain, comprising LCDR1, LCDR2 and LCDR3 having a sequence as shown in SEQ ID NO: 4, 5 and 6, respectively, or comprising LCDR1, LCDR2 and LCDR3 having a sequence at least 80%, 85%, 90%, 92%, 95%, 97%, 98%, 99% or higher identity to SEQ ID NO: 4, 5 and 6 respectively, or comprising LCDR1, LCDR2 and LCDR3 having a sequence as shown in SEQ ID NO: 4, 5 and 6 respectively except for one or more amino acid substitutions (for example conservative substitutions).

More preferably, the first single chain Fv comprises:
(1) a VH domain having an amino acid sequence as shown in SEQ ID NO: 7, or having a sequence at least 80%, 85%, 90%, 92%, 95%, 97%, 98%, 99% or higher identity to SEQ ID NO: 7, or having a sequence as shown in SEQ ID NO: 7 except for one or more amino acid substitutions (for example conservative substitutions); and
(2) a VL domain having an Amino acid sequences as shown in SEQ ID NO: 8, or having a sequence at least 80%, 85%, 90%, 92%, 95%, 97%, 98%, 99% or higher identity to SEQ ID NO: 8, or having a sequence as shown in SEQ ID NO: 8 except for one or more amino acid substitutions (for example conservative substitutions). Wherein, the linker peptide L2 connecting the first single chain Fv and the second single chain Fv of the present invention composes of a flexible peptide and a rigid peptide.

Further, the flexible peptide comprises two or more amino acids, and is preferably selected from the following amino acids: Gly(G), Ser(S), Ala(A) and Thr(T). More preferably, the flexible peptide comprises G residues and S residues. Most preferably, the general structural formula of amino acid composition of the flexible peptide is GxSy(GGGGS (SEQ ID NO: 22))z, wherein x, y and z are integers greater than or equal to 0, and x+y+z is ≥1. For example, in a preferred embodiment, an amino acid sequence of the flexible peptide is G2(GGGGS)$_3$ (SEQ ID NO: 29).

Further, the rigid peptide is a full-length sequence consisting of amino acids at positions 118 to 145 derived from the carboxyl terminal of natural human chorionic gonadotropin beta subunit (as shown in SEQ ID NO: 9) or a truncated fragment thereof (hereinafter collectively referred to as CTP). preferably, CTP1 rigid peptide comprises 10 amino acids at the N-end of SEQ ID NO: 9, namely SSSSKAPPPS (SEQ ID NO: 24); or CTP2 rigid peptide comprises 14 amino acids at the C end of SEQ ID NO: 9, namely SRLPGPSDTPILPQ (SEQ ID NO: 25); CTP3 rigid peptide comprises 16 amino acids at the N end of SEQ ID NO: 9, namely SSSSKAPPPSLPSPSR (SEQ ID NO: 26); CTP4 rigid peptide comprises 28 amino acids and starts at position 118 of human chorionic gonadotropin f subunit and ends at position 145, namely SSSSKAPPPSLPSPSRLPGPSDTPILPQ (SEQ ID NO: 27).

In a preferred embodiment of the present invention, the rigid peptide is SSSSKAPPPS (SEQ ID NO: 24), namely, CTP1 rigid peptide. In other preferred implementations, the rigid peptide sequence further comprises CTP2 (SRLPGPSDTPILPQ (SEQ ID NO: 25)), CTP3 (SSSSKAPPPSLPSPSR (SEQ ID NO: 26)), CTP4 (SSSSKAPPPSLPSPSRLPGPSDTPILPQ (SEQ ID NO: 27)).

In a preferred embodiment of the present invention, an amino acid sequence of the linker peptide L2 is shown in SEQ ID NO: 10, the amino acid of its flexible peptide composed of G2(GGGGS)$_3$ (SEQ ID NO: 29), and the amino acid of its rigid peptide composed of SSSSKAPPPS (SEQ ID NO: 24), namely, CTP1 rigid peptide.

Wherein, the second single chain Fv of bispecific antibody specifically binds to CD3 and binds to effector cells with an $EC_{50}$ value greater than 50 nM, or greater than 100 nM, or greater than 300 nM, or greater than 500 nM in vitro FACS binding analysis; more preferably, the second single chain Fv of the bispecific antibody can not only bind to human CD3, but also specifically bind to CD3 of a cynomolgus monkey or a rhesus monkey. In a preferred embodiment of the present invention, the bispecific antibody specifically binds to effector cells with an $EC_{50}$ value of 132.3 nM.

Preferably, the second single chain Fv comprises:
(1) a VH domain, comprising HCDR1, HCDR2 and HCDR3 having a sequence as shown in SEQ ID NO: 11, 12 and 13 respectively, or comprising HCDR1, HCDR2 and HCDR3 having a sequence at least 80%, 85%, 90%, 92%, 95%, 97%, 98%, 99% or higher identity to SEQ ID NO: 11, 12 and 13 respectively, or comprising HCDR1, HCDR2 and HCDR3 having a sequence as shown in SEQ ID NO: 11, 12 and 13 respectively except for one or more amino acid substitutions (for example conservative substitutions); and (2) a VL domain, comprising LCDR1, LCDR2 and LCDR3 having a sequence as shown in SEQ ID NO: 14, 15 and 16, respectively, or comprising LCDR1, LCDR2 and LCDR3 having a sequence at least 80%, 85%, 90%, 92%, 95%, 97%, 98%, 99% or higher identity to SEQ ID NO: 14, 15 and 16 respectively, or comprising LCDR1, LCDR2 and LCDR3 having a sequence as shown in SEQ ID NO: 14, 15 and 16 respectively except for one or more amino acid substitutions (for example conservative substitutions).

More preferably, the second single-chain Fv comprises a VH domain, having an amino acid sequence as shown in SEQ ID NO: 17 or a sequence at least 80%, 85%, 90%, 92%, 95%, 97%, 98%, 99% or higher identity to SEQ ID NO: 17 or having a sequence as shown in SEQ ID NO: 17 except for one or more amino acid substitutions (for example conservative substitutions); and A VL domain, having an amino acid sequence as shown in SEQ ID NO: 18 or having a sequence at least 80%, 85%, 90%, 92%, 95%, 97%, 98%, 99% or higher identity to SEQ ID NO: 18 or having a sequence as shown in SEQ ID NO: 18 except for one or more amino acid substitutions (for example conservative substitutions).

Preferably, the VH domain and VL domain of the second single-chain Fv are connected by a linker peptide L3, and the VH, L3 and VL are arranged in the order of VH-L3-VL or VL-L3-VH, and amino acid sequence of the linker peptide L3 is (GGGGX (SEQ ID NO: 23))n, wherein, x is selected from Ser or Ala, and n is a natural number from 1-5; preferably X is Ser, preferably n is 3.

In a preferred embodiment of the present invention, an amino acid sequence of the linker peptide L3 is (GGGGS (SEQ ID NO: 22))$_3$, in other preferred embodiments, an amino acid sequence of the linker peptide L3 further comprises (GGGGS (SEQ ID NO: 22))$_1$ or (GGGGS (SEQ ID NO: 22))$_2$ or (GGGGS (SEQ ID NO: 22))$_4$ or (GGGGS (SEQ ID NO: 22))$_5$ or (GGGGA (SEQ ID NO: 28))$_1$ or (GGGGA (SEQ ID NO: 28))$_2$ or (GGGGA (SEQ ID NO: 28))$_3$ or (GGGGA (SEQ ID NO: 28))$_4$ or (GGGGA (SEQ ID NO: 28))$_5$.

Wherein, the Fc fragment of the present invention is connected with the second single-chain Fv directly or through a linker peptide L4, and the linker peptide L4 comprises 1-20 amino acids, and is preferably selected from the following amino acids: Gly(G), Ser(S), Ala(A) and Thr(T); more preferably, the linker peptide L4 is selected from Gly(G) and Ser(S); more preferably, the linker peptide L4 is composed of (GGGGS (SEQ ID NO: 22))n, and n=1, 2, 3 or 4. In a preferred embodiment of the present invention, the Fc fragment is directly connected to the second single chain Fv. In another prefer embodiment, that Fe fragment is connected with the second single chain Fv through a linker peptide L4, and the amino acid sequence of the connected peptide L4 comprises (GGGGS (SEQ ID NO: 22))$_1$ or (GGGGS (SEQ ID NO: 22))$_2$ or (GGGGS (SEQ ID NO: 22))$_3$ or (GGGGS (SEQ ID NO: 22))$_4$.

The Fc fragment of the present invention comprises hinge region, CH2 and CH3 domain derived from a human immunoglobulin heavy chain constant region, for example, in some implementations, the Fc fragment of the present invention is derived from heavy chain constant region selected from human IgG1, IgG2, IgG3, IgG4, IgM, IgA1, IgA2, IgD and IgE; particularly selected from heavy chain constant regions for example human IgG1, IgG2, IgG3 and IgG4, more particularly selected from heavy chain constant regions of human IgG1 or IgG4; and, the Fc fragment has one or more amino acid substitutions, deletions or additions (for example, at most 20, at most 15, at most 10, or at most 5 substitutions, deletions or additions) compared with an original natural sequence thereof.

The Fc fragment has an amino acid sequence as shown in SEQ ID NO: 19, and compared with an original natural sequence of the Fc fragment, of the Fc fragment has the following 6 amino acid replacements or substitutions determined according to the EU numbering system: L234A/L235A/N297A/P331S/T250Q/M428L; and K447 determined according to EU numbering system is deleted or deleted. The EU numbering system comes from the website: http://www.imgt.org/imgtscientific chart/numbering/Hu_iggnber.htm.

In some preferred Implementations, the Fc fragment is altered, e.g., mutated, to modify the properties of the bispecific antibody molecule of the present invention (e.g., change one or more of the following characteristics: Fc receptor binding, antibody glycosylation, effector cell function or complement function).

For example, the bispecific antibody provided by the present invention comprises Fc variants with amino acid substitutions, deletions, or additions with altered effector functions (e.g., reduction or elimination). The Fc region of antibody mediates several important effector functions, for example ADCC, ADCP, CDC, etc. The method of changing effector functions by replacing amino acid residues in the Fc region of antibody to change the affinity of antibody to effector ligand (such as FcγR or complement C1q) is known in the art (see, for example, EP 388,151A1; US 564,8260; US 562,4821; Natsume A et al., Cancer Res., 68: 3863-3872, 2008; Idusogie E E et al., J. Immunol., 166: 2571-2575, 2001; Lazar G A et al., PNAS, 103: 4005-4010, 2006; Shields R L et al., JBC, 276: 6591-6604, 2001; Stavenhagen J B et al., Cancer Res., 67: 8882-8890, 2007; Stavenhagen J B et al., Advan. Enzyme. Regul., 48: 152-164, 2008; Alegre M L et al., J. Immunol., 148: 3461-3468, 1992; and Kaneko E et al., Biodrugs, 25: 1-11, 2011). In some preferred embodiments of the present invention, the amino acid L235 (EU numbering) in the antibody constant region is modified to change the Fc receptor interaction, for example L235ε or L235A. In another preferred embodiments, amino acids 234 and 235 in the antibody constant region are modified at the same time, such as L234A and L235A (L234A/L235A) (EU numbering).

For example, the bispecific antibody provided by the present invention can comprise Fc variants with amino acid substitution, deletion, or addition with prolonged circulating half-life. M252Y/S254T/T256E, M428L/N434S or T250Q/M428L can prolong the half-life of antibody in primates. See Chinese invention patents CN 201280066663.2, US 2005/0014934A1, WO 97/43316, U.S. Pat. Nos. 5,869,046, 5,747,003 and WO 96/32478 for more mutation sites comprised in Fc variants with enhanced binding affinity to neonatal receptor (FcRn). In some preferred embodiments of the present invention, amino acid M428 (EU numbering) in the antibody constant region is modified to enhance the binding affinity of FcRn receptor, for example M428L. In another preferred embodiments, amino acids 250 and 428(EU numbering) in the antibody constant region are modified at the same time, for example T250Q and M428L(T250Q/M428L).

For example, the bispecific antibody provided by the present invention can further comprise Fc variants with amino acid substitutions, deletions, or additions that can reduce or eliminate Fc glycosylation. For example, Fc variants comprise reduced glycosylation of N-linked glycans normally present at amino acid position 297 (EU numbering). Glycosylation at N297 has great influence on the activity of IgG. if glycosylation at N297 is removed, it will affect the conformation of the upper half part of CH2 of IgG molecule, thus losing the binding ability to FcγRs and affecting the biological activity of antibody. In some preferred embodiments of the present invention, amino acid N297 (EU numbering) in the constant region of human IgG is modified to avoid glycosylation of antibody, for example N297A.

For example, the bispecific antibody provided by the present invention can further comprise Fc variants with amino acid substitution, deletion, or addition to eliminate charge heterogeneity. Many post-translational modifications in the expression process of engineering cells will cause charge heterogeneity of monoclonal antibodies, and the heterogeneity of lysine at the C-terminal of IgG antibody is one of the main reasons, lysine K at the C-terminal of heavy chain may be missing in a certain proportion during antibody production, resulting in charge heterogeneity, thus affecting the stability, effectiveness, immunogenicity or pharmacokinetics of antibodies. In some preferred embodiments of the present invention, K447 (EU numbering) at the C-terminal of IgG antibody is removed or deleted, so as to eliminate the charge heterogeneity of the antibody and improve the uniformity of the expression product.

Compared with the bispecific antibody including wild-type human IgG Fc region, the Fc fragment comprised in the bispecific antibody provided by the present invention shows reduced affinity for at least one of human FcγRs (FcγRI, FcγRIIa or FcγRIIIa) and C1q, and has reduced effector cell function or complement function. For example, in a preferred embodiment of the present invention, the Fc fragment comprised in the bispecific antibody is derived from human IgG1, and has L234A and L235A substitutions (L234A/L235A), showing reduced binding ability to FcγRI; in addition, the Fc fragment contained in the bispecific antibody provided by the present invention may further comprise amino acid substitutions that change one or several other characteristics (for example, binding ability with FcRn receptor, antibody glycosylation or antibody charge heterogeneity, etc.). For example, in a preferred embodiment of the present invention, the amino acid sequence of the Fc fragment is shown as SEQ ID NO: 19, which has the amino acid replacement or substitution of L234a/L235a/T250Q/N297a/P331s/M428L compared with an original natural sequence thereof, and K447 is deleted or deleted.

The bispecific antibody molecule of the present invention is formed by combining two identical polypeptide chains through interchain disulfide bonds in hinge regions of Fc fragments to form a tetravalent homodimer, and each polypeptide chain consists of an anti-BCMA scFv, a linker peptide, an anti-CD3 scFv and an Fc fragment in sequence from the N end to the C end.

In a preferred embodiment of the present invention, the bispecific antibody binds to human BCMA and CD3, and its amino acid sequence is as follows:
(1) sequence shown in SEQ ID NO: 20;
(2) Compared with the sequence shown in SEQ ID NO: 20, the sequence having one or several substitutions, deletions or additions (for example, one, two, three, four or five substitutions, deletions or additions); or
(3) sequence having at least 80%, at least 85%, at least 90%, at least 91%, at least 92%, at least 93%, at least 94%, at least 95%, at least 96%, at least 97%, at least 98%, at least 99% or 100% sequence identity to the sequence shown in SEQ ID NO: 20.

In certain preferred implementations, the substitutions described in (2) are conservative substitutions.

In a second aspect of the present invention, there is provided a DNA molecule encoding the foregoing bispecific antibody.

In a preferred embodiment of the present invention, the DNA molecule encoding the foregoing bispecific antibody has a nucleotide sequence shown in SEQ ID NO: 21.

In a third aspect of the present invention, there is provided a vector comprising the foregoing DNA molecule.

According to a fourth aspect of the present invention, there is provided a host cell comprising the foregoing vector; the host cell comprise a prokaryotic cell, a yeast cell or a mammalian cell, preferably said host cell is a mammalian cell, such as a CHO cell, a NS0 cell or a other mammalian cell, more preferably a CHO cell.

According to a fifth aspect of the present invention, there is provided a pharmaceutical composition comprising the foregoing bispecific antibody and a pharmaceutically acceptable excipient and/or vector and/or diluent.

In a sixth aspect of the present invention, there is also provided a method for preparing the bispecific antibody of the present invention, comprises:
(a) obtaining fusion gene of bispecific antibody, construct the expression vector of bispecific antibody;
(b) transfecting the foregoing expression vector into a host cell by a genetic engineering method;
(c) culturing the foregoing host cell under conditions that allow the production of the bispecific antibody;
(d) Separating and purifying the produced antibody.

Wherein, the expression vector in step (a) is selected from one or more of plasmids, bacteria and viruses, preferably, the expression vector is a plasmid, more preferably, the expression vector is PCDNA3.1;

Wherein, in the step (b), the constructed vector is transfected into a host cell by a genetic engineering method, the host cell comprises a prokaryotic cell, a yeast cell or a mammalian cell, preferably, the host cell is a mammalian cell such as a CHO cell, a NS0 cell or a other mammalian cell, more preferably a CHO cell.

Wherein, in step (d), the bispecific antibody is separated and purified by conventional immunoglobulin purification methods including protein A affinity chromatography and ion exchange, hydrophobic chromatography, or molecular sieve method.

The seventh aspect of the present invention, providing the use of the bispecific antibody in the manufacture of a medicament for treating or improving a plasma cell disorder, an other B cell disorder associated with BCMA expression, or an autoimmune disease, wherein the plasma cell disorder includes but is not limited to multiple myeloma, plasmacytoma, plasma cell leukemia, macroglobulinaemia, amyloidosis, Waldenstrom's macroglobulinaemia, solitary bone plasmacytoma, extramedullary plasmacytoma, osteosclerotic myeloma, heavy chain disease, monoclonal gammopathy of undetermined significance and smoldering multiple myeloma.

According to the technical scheme disclosed by the present invention, beneficial technical effects are achieved:
1, the bispecific antibody provided by the present invention is not easy to bind to normal cells with weak or low expression of BCMA, which reduces nonspecific killing, but the binding specificity to cells with overexpression or high expression of BCMA does not decrease significantly, showing a good killing effect in vivo. This is also known, it is known that when the target antigen is only expressed on tumor cells or the bispecific antibody of the present invention is only specifically combined with tumor cells overexpressing the target antigen, the immune effector cells are only activated in the target cell tissues, which makes the nonspecific killing of normal cells and the accompanying release of cytokines by the bispecific antibody be minimized, thus reducing its toxic and side effects in clinical treatment.

2, the anti-CD3 scFv selected by the bispecific antibody provided by the present invention specifically binds to effector cells with weak binding affinity ($EC_{50}$ value is greater than 50 nM, or greater than 100 nM, or greater than 300 nM, or greater than 500 nM). in addition, the CTP rigid peptide comprised in the linker peptide L3 embedded between the anti-BCMA scFv and Fc and located at its n terminal and the Fc fragment located at its c terminal, they all partially "cover" or "shield" the antigen binding domain of anti-CD3 scFv, and this steric effect makes it bind to CD3 with weaker binding affinity (for example, more than 1 μM), which weakens its ability to stimulate the activation of t cells, thus limiting the excessive release of cytokines, thus having higher safety.

3, the bispecific antibody provided by the present invention creatively adopts bivalent anti-CD3 scFv, which makes the bispecific antibody avoid the asymmetric structure of heterodimer type (the comprised anti-CD3 scFv is monovalent) generally adopted in the prior art in configuration design, so that the problem of mismatch between heavy chains does not exist, and the downstream purification steps are simplified; and unexpectedly, the nonspecific binding of anti-CD3 scFv to T cells was not observed in the in vitro cell binding test, and the degree of cell activation (release of cytokines such as IL-2) was controlled within a safe and effective range, that is, the bivalent anti-CD3 scFv structure adopted in the present invention did not cause over-activation of t cells independently of antigen, but for other bispecific antibodies containing bivalent anti-CD3 domain, T cells were uncontrollable.

4, the modified Fc fragment comprised in the bispecific antibody provided by the present invention does not have the ability of FcγR binding, which avoids the systemic activation of T cells mediated by FcγR, thus allowing immune effector cells to be activated only in target cell tissues.

5, the bispecific antibody provided by the present invention is homodimeric, does not have the problem of mismatch between heavy chain and light chain, and has stable downstream production process, simple and efficient purification steps, uniform expression products, and obviously improved physicochemical and in vivo stability.

DETAILED DESCRIPTION OF THE INVENTION

Abbreviations and Definitions

BCMA B cell maturation antigen
BiAb bispecific antibody (bispecific antibody) CDR Complementarity determining regions in immunoglobulin variable regions
defined by a Kabat numbering system
$EC_{50}$ A concentration that produces 50% efficacy or binding
ELISA enzyme-linked immunosorbent assay
FR Antibody framework region: immunoglobulin variable region excluding CDR region
HRP horse radish peroxidase
IL-2 interleukin2
IFN interferon
$IC_{50}$ A concentration that produces a 50% inhibitory
IgG immune globulinG
Kabat Immunoglobulin alignment and numbering system advocated by Elvin A Kabat
mAb monoclonal antibody
PCR polymerase chain reaction
V-region IgG chain segments with variable sequence between different antibodies It extends to the 109th Kabat residue of the light chain and the 113th residue of the heavy chain
VH immunoglobulin heavy chain variable region
VK Immunoglobulin κ light chain variable region
$K_D$ equilibrium dissociation constant
$k_a$ association rate constant
$k_d$ dissociation rate constant In the present invention, unless indicated otherwise, the scientific and technical terms used herein have the meanings commonly understood by those skilled in the art. The antibodies or fragments thereof used in the present invention can use conventional techniques known in the art individually or in combination (e.g., amino acid deletion, insertion, substitution, addition, and/or recombination and/or other modification methods) to be further modified. The method of introducing such modification into its DNA sequence based on amino acid sequence of an antibody is well known to those skilled in the art; See, for example, Sambrook, molecular cloning: A Laboratory Manual, Cold Spring Harbor Laboratory (1989) N.Y.. The modifications referred to are preferably performed at the nucleic acid level. Meanwhile, in order to better understand the present invention, definitions and explanations of related terms are provided below.

"BCMA" is a B cell maturation antigen, belonging to tumor necrosis factor receptor superfamily member, which is preferably expressed in mature B lymphocytes and expressed on the surface of plasmablasts (i.e., plasma cell precursors) and plasma cells. RNA of BCMA can be detected in spleen, lymph node, thymus, adrenal gland and liver, the level of BCMA mRNA in multiple B cell lines also increased after maturation. BCMA is associated with many diseases (leukemia, lymphoma (such as Hodgkin's lymphoma), multiple myeloma, autoimmune diseases (such as systemic lupus erythematosus) and so on, so it can be used as a potential target for related B cell diseases. Indications for BCMA targets further comprises other associated diseases or disorders found in the prior art and found in the future. This term further comprises any variant, isoform, and species homologue of BCMA, which is expressed naturally by cells, comprising tumor cells, or expressed by cells transfected with BCMA gene or cDNA.

CD3 molecules is an important differentiation antigen on T cell membrane, a characteristic marker of mature T cells, composed of six peptide chains, which form TCR-CD3 complex with non-covalent bond and T cell antigen receptor (TCR), it not only participates in the intracytoplasmic assembly of the TCR-CD3 complex, but also transmits antigen stimulation signals through the immune receptor tyrosine-based activation motif (Immunoreceptor Tyrosine-based Activation Motif, ITAM) in the cytoplasmic region of each polypeptide chain. The main functions of CD3 molecule are to stabilize TCR structure, transmit T cell activation signal, when TCR specifically recognizes and binds to antigen, CD3 participates in signal transduction to T cell cytoplasm, which is the first signal to induce T cell activation, playing an extremely important role in T cell antigen recognition and immune response.

"CD3" refers to as a part of T cell receptor complex, which is composed of three different chains: CD3δ, CD3δ and CD3γ. The clustering of CD3 on T cells through for example, the immobilization of anti-CD3 antibodies, leads to the activation of T cells, which is similar to tT cell receptor-mediated activation, but independent of the specificity of TCR clones. Most anti-CD3 antibodies recognize CD3 ε chain. The second functional domain of the present invention specifically recognizing T cell surface receptor CD3 is not particularly limited as long as it can specifically recognize CD3, for example but not limited to CD3 antibodies mentioned in the following patents: U.S. Pat. Nos. 7,994,289; 6,750,325; 6,706,265; 5,968,509; 8,076,459; 7,728,114; US20100183615. Preferably, the anti-human CD3 antibodies used in the present invention are cross-reactive with cynomolgus monkey and/or rhesus monkeys, for example, but not limited to, the anti-human CD3 antibodies mentioned in the following patents: WO 2016130726, US 20050176028, WO 2007042261 or WO 2008119565. This term further comprises any CD3 variants, isoforms, derivatives and species homologues, which is naturally expressed by cells or expressed on cells transfected with genes or cDNA encoding the aforementioned chains.

The term "antibody" specifically comprises monoclonal antibodies, polyclonal antibodies and antibody-like polypeptides, for example chimeric antibodies and humanized antibody. "Antigen binding fragment" comprises fragments provided by any known techniques, for example enzymatic cleavage, peptide synthesis and recombination techniques. Some antigen-binding fragments are composed of intact antibody parts that retain the antigen-binding specificity of the parent antibody molecules. For example, an antigen binding fragment may comprise at least one variable region (heavy chain or light chain variable region) or one or more CDRs of an antibody known to bind a specific antigen. Examples of suitable antigen binding fragments include, but are not limited to, bispecific antibody bodies and single chain molecules as well as Fab, F(ab')$_2$, Fc, Fabc and Fv molecules, single chain (Sc) antibodies, separate antibody light chains, separate antibody heavy chains, chimeric fusions between antibody chains or CDRs and other protein, protein scaffolds, heavy chain monomers or dimers, light chain monomers or dimers, a dimer consisting of one heavy chain and one light chain, a monovalent antibody consisting of the VL, VH, CL, and CH1 domains, or as described in WO2007059782, comprises a bivalent fragment of two Fab fragments connected by a disulfide bond on a hinged region, a Fd fragment consisting substantially of VH and CH1 domains; Fv fragment, dAb fragment, which is substantially composed of VL and VH domains of the single arm of the antibody (Ward et al., Nature, 1989, 341: 544-54), it substantially consists of VH domain, also called domain antibody (Holt et al., Trends Biotechnology. 2003, 21 (11): 484-90); or nanoparticles (Revets et al.; Expert Opin Biol Ther.2005 Jan; 5(1): 111-24); Isolated complementarity determining regions (CDRs), etc. All antibody isotypes can be used to produce antigen binding fragments. Additionally, antigen binding fragments may comprise a non-antibody protein framework, which can successfully incorporate polypeptide fragments into an orientation that confers affinity to a given antigen of interest (for example a protein scaffold). The antigen-binding fragment can be recombinantly produced or produced by enzymatic or chemical cleavage of an intact antibody. The term "antibody or antigen binding fragment thereof" may be used to represent that a given antigen binding fragment is incorporated into one or more amino acid fragments of the antibody mentioned in the phrase.

The term "hypervariable region" or "CDR region" or "complementarity determining region" refers to an antibody amino acid residue responsible for antigen binding, which is a discontinuous amino acid sequence. A CDR region sequence may be defined by the IMGT, Kabat, Chothia and AbM methods or the amino acid residues within the variable region identified by any CDR region sequence determination method well known in the art. For example, the hypervariable region comprises the following amino acid residues: amino acid residues from the "complementarity determining region" or "CDR" defined by sequence alignment, for example, residues 24-34 (L1), 50-56 (L2) and 89-97 (L3) of the light chain variable domain and residues 31-35 (H1), 50-65 (H2) and 95-102 (H3) of the heavy chain variable domain See Kabat et al., 1991, sequences of proteins of immunological interest, 5th edition, Public Health Service, National Institutes of Health, Bethesda, Md.; and/or residues from the "hypervariable ring" (HVL) defined according to structure, for example, residues 26-32 (L1), 50-52 (L2) and 91-96 (L3) of the light chain variable domain and residues 26-32 (H1), 53-55 (H2) and 96-101 (H3) of the heavy chain variable domain, see Chothia and Leskl, J.Mol.Biol., 196: 901-917, 1987. A "framework" residue or "FR" residue is a variable domain residue other than a hypervariable region residue as defined herein. In certain implementations, the CDR contained in the antibody or antigen binding fragment of the present invention is preferably determined by Kabat, Chothia or IMGT numbering system. Those skilled in the art can explicitly confer each system to any variable domain sequence without relying on any experimental data beyond the sequence itself. For example, the numbering of Kabat residues of a given antibody can be determined by comparing the antibody sequence with each "standard" numbering sequence. Based on the sequence numbers provided herein, it is completely within the conventional technical scope of those skilled in the art to determine the numbering scheme of any variable region sequence in the sequence list.

The term "single chain Fv antibody" (or "scFv antibody") refers to an antibody fragment including VH and VL domains of an antibody, which is a recombinant protein of a heavy chain variable region (VH) and a light chain variable region (VL) connected by a linker, the linker makes these two domains cross-link to form an antigen binding site, the linker sequence is generally composed of a flexible peptide, for example but not limited to G2(GGGGS)$_3$ (SEQ ID NO: 29). ScFv is generally ⅙ the size of an intact antibody. The single chain antibody is preferably an amino acid chain sequence encoded by a nucleotide chain. For a review of scFv, see PluckThun (1994) The Pharmacology of Monoclonal Antibodies, Vol. 113, Rosenburg and Moore, Springer-Verlag, New York, pp. 269-315. See also international patent application publication no. WO 88/01649 and U.S. Pat. Nos. 4,946,778 and 5,260,203.

The term "Fab fragment" consists of CH1 and variable regions of one light chain and one heavy chain. The heavy chain of Fab molecule cannot form disulfide bond with another heavy chain molecule. The size of "Fab antibody" is ⅓ of that of a intact antibody, it comprises only one antigen binding site.

The term "Fab' fragment" contains VH domain and CH1 domain of one light chain and one heavy chain, and the constant region part between CH1 and CH2 domain.

The term "F(ab')$_2$ fragment" contains VH and CH1 domains of two light chains and two heavy chains, and the constant region part between CH1 and CH2 domains, thereby forming an interchain disulfide bond between the two heavy chains. Therefore, the F(ab')$_2$ fragment consists of two Fab' fragments held together by disulfide bonds between two heavy chains.

The term "Fc" region refers to antibody heavy chain constant region fragment, which comprises at least hinge region, CH2 and CH3 domain.

The term "Fv region" comprises variable regions from both heavy and light chains, but lacks constant regions, is the smallest fragment including intact antigen recognition and binding sites.

The term "Fd fragment" is composed of CH1 and variable region of a heavy chain, which is the heavy chain part left after light chain is removed from Fab fragment.

The term "disulfide bond stability protein (dsFv)" introduces one cysteine mutation point in the VH and VL regions respectively, thereby forming a disulfide bond between VH and VL to achieve structural stability.

The term "linker peptide" refers to a peptide connecting two polypeptides, wherein the linker peptide can be two immunoglobulin variable regions or one variable region. The length of the linker peptide may be 0-30 amino acids or 0-40 amino acids. In some implementations, the linker peptide may be 0-25, 0-20, or 0-18 amino acids in length. In some implementations, the linker peptide may be a peptide no more than 14, 13, 12, 11, 10, 9, 8, 7, 6 or 5 amino acids long. In other implementations, the linker peptide may be 0-25, 5-15, 10-20, 15-20, 20-30 or 30-40 amino acids long. In other implementations, the linker peptide may be about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids long. linker peptides are known to those skilled in the art. The linker peptide may be prepared by any method in the art. For example, the linker peptide may be of synthetic origin.

The term "heavy chain constant region" comprises amino acid sequences derived from immunoglobulin heavy chains. Polypeptides including heavy chain constant regions comprise at least one of CH1 domain, hinge (e.g., upper hinge region, middle hinge region, and/or lower hinge region) domain, CH2 domain, CH3 domain, or variants or fragments thereof. For example, the antigen-binding polypeptide used in the present application can comprise a polypeptide chain with a CH1 domain; polypeptides with CH1 domain, at least a part of hinge domain and CH2 domain; Polypeptide chain with CH1 domain and CH3 domain; a polypeptide chain with CH1 domain, at least a part of hinge domain and CH3 domain, or a polypeptide chain with CH1 domain, at least a part of hinge structure, CH2 domain and CH3 domain. In another embodiment, the polypeptide of the present application comprises a polypeptide chain having a CH3 domain. Additionally, antibodies used in the present application may lack at least a part of the CH2 domain (e.g., all or a part of the CH2 domain). As mentioned foregoing, it should be understood by those of ordinary skill in the art that the heavy chain constant regions may be modified so that they are different from naturally occurring immunoglobulin molecules in amino acid sequence.

The term "light chain constant region" comprises the amino acid sequence from the antibody light chain. Preferably, the light chain constant region comprises at least one of a constant kappa domain and a constant lambda domain.

The term "VH domain" comprises the amino terminal variable domain of immunoglobulin heavy chain, while the term "CH1 domain" comprises the first (mostly amino terminal) constant region of immunoglobulin heavy chain. CH1 domain is adjacent to VH domain and is the amino terminus of hinge region of immunoglobulin heavy chain molecule.

The term "hinge region" comprises that part of the heavy chain molecule that connects the CH1 domain to the CH2 domain. The hinge region contains about 25 residues and is flexible so that the two N-terminal antigen binding regions move independently. The hinge region can be divided into three different domains: upper, middle and lower hinge domains (Roux K H et al., J.Immunol., 161: 4083, 1998).

The term "disulfide bond" comprises a covalent bond formed between two sulfur atoms. Amino acid cysteine contains sulfhydryl group, which can form disulfide bond or bridge with the second sulfhydryl group. In most naturally occurring IgG molecules, CH1 and CK regions are connected by disulfide bonds and two heavy chains are connected by two disulfide bonds at 239 and 242 (position 226 or 229, EU numbering system) corresponding to the Kabat numbering system.

"Binding" defines the affinity interaction between a specific epitope on an antigen and its corresponding antibody, which is generally understood as "specific recognition". "Specific recognition" means that the bispecific antibody of the present invention does not cross-react with or does not substantially cross-react with any polypeptide other than the target antigen. And the degree of specificity may be judged by immunological techniques, including but not limited to immunoblotting, immunoaffinity chromatography, flow cytometry and the like. In the present invention, the specific recognition preference is determined by flow cytometry, while the standard of specific recognition in specific cases can be judged by the general technical personnel in the field according to their knowledge of the field.

The term "bispecific antibody" refers to the bispecific antibody of the present invention, for example anti-Her2 antibody or antigen binding fragment thereof, can be derivatized or connected to another functional molecule, for example another peptide or protein (e.g., TAA, cytokines and cell surface receptors) to generate bispecific molecules that bind to at least two different binding sites or target molecules. To create a bispecific molecule of the present invention, an antibody of the present invention may be functionally connected (e.g., by chemical coupling, gene fusion, non-covalent binding, or other means) to one or more other binding molecules, such as another antibody, antibody fragment, peptide, or binding mimetic, thereby producing a bispecific molecule. For example, a "bispecific antibody" means that contains two variable domains or scFv units so that the resulting antibody recognizes two different antigens. Many different forms and uses of bispecific antibodies are known in the art (Chames P et al., curr. opin. drug disc. dev., 12: 276, 2009; Spiess C et al., Mol. Immunol., 67: 95-106, 2015).

The term "hCG-β carboxy terminal peptide (CTP)" is a short peptide from the carboxy terminal of β subunit of human chorionic gonadotropin (hCG). The four polypeptide hormones associated with reproduction, follicle-stimulating hormone (FSH), luteinizing hormone (LH), thyroid stimulating hormone (TSH) and chorionic gonadotropin (hCG), contain the same α-subunit and their respective specific β-subunit. Compared with the other three hormones, the in vivo half-life of hCG is obviously prolonged, which is mainly derived from the specific carboxyl terminal peptide (CTP) on its β-subunit. CTP contains 37 amino acid residues with 4 O-glycosylation sites, the terminal of the sugar side chain is sialic acid residues. Negatively charged, highly salivated CTP is capable of resisting renal clearance, thereby prolonging the in vivo half-life of the protein (Fares F A et al., Proc. Natl. Acad. Sci. USA, 89: 4304-4308, 1992).

The term "glycosylation" means that oligosaccharides (carbohydrates containing two or more monosaccharides connected together, for example 2 to about 12 monosaccharides connected together) attach to form glycoproteins. Oligosaccharide side chains are usually connected to the backbone of glycoproteins by N- or O-linkage. Oligosaccharides of the antibodies disclosed herein are usually connected to the CH2 domain of the Fc region as N-linked oligosaccharides. "N-linked glycosylation" refers to the carbohydrate moieties linked to the asparagine residues of glycoprotein chains. For example, the skilled person can recognize that each of CH2 domains of mouse IgG1, IgG2a, IgG2b and IgG3 and human IgG1, IgG2, IgG3, IgG4, IgA and IgD has a single site for N-linked glycosylation at residue 297.

In yet aspect, the amino acid sequence comprised in the heavy chain and light chain variable regions which comprised in the antibody of the present invention that are homologous to the amino acid sequences of the preferred antibodies described herein, and wherein the antibody retains the desired functional characteristics of the Her2×CD3 bispecific antibody described in the present invention.

Antibodies with conservative modification, the term "conservative modification" is intended to mean that amino acid modification will not significantly affect or change the binding features of antibodies containing the amino acid sequence. Such conservative modifications comprise amino acid substitutions, additions and deletions. Modifications can be introduced into the antibodies of the present invention by standard techniques known in the art, for example site-directed mutagenesis and PCR-mediated advantages. Conservative amino acid substitution refers to the substitution of an amino acid residue with an amino acid residue having a similar side chain. Families of amino acid residues having similar side chains are described in detail in the art. These families comprise amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Therefore, one or more amino acid residues in the CDR region of the antibody of the present invention can be replaced with other amino acid residues from the same side chain family.

An Fc variant with altered binding affinity for the neonatal receptor (FcRn), as used here, "FcRn" refers to a protein encoded at least in part by the FcRn gene that binds to the Fc region of an IgG antibody. The FcRn can be derived from any organism including but not limited to human, mouse, rat, rabbit and monkey. The functional FcRn protein comprises two chains, often referred to as heavy and light chains, the light chain is β-2-microglobulin and the heavy chain is encoded by the FcRn gene.

The present invention relates to a binding regulated antibody to FcRn (regulation comprises increasing as well as decreasing binding). For example, in some cases, increased binding will cause cells to recycle antibodies, and thus prolonging for example, the half-life of therapeutic antibodies. Sometimes it is desirable to reduce FcRn binding, for example serves as a diagnostic or therapeutic antibody including a radiolabel. Additionally, antibodies showing increased binding to FcRn while altered binding to other Fc receptors, for example Fcγ Rs, can be used in the present invention.

The application involves to antibodies including amino acid modifications that modulate the binding force to FcRn. It is of special significance that the binding affinity for FcRn is shown to increase at lower pH, whereas at higher pH the binding shows little change in the minimal incorporation of antibodies or their functional variants in the Fc domain.

The Fc variant with enhanced binding affinity to neonatal receptor (FcRn), whose plasma half-life depends on its binding to FcRn, generally binds at pH 6.0 and dissociates at pH 7.4 (plasma pH). Through the study of the binding sites of the both, the binding site of IgG on FcRn was modified to increase its binding ability at pH 6.0. It has been proved that mutations in some residues of human Fcγ domain which are important for binding FcRn can increase serum half-life. Mutations in T250, M252, S254, T256, V308, E380, M428, and N434(EU Nos.) have been reported to increase or decrease FcRn binding affinity (Roopenian D C et al., Nat. Rev. Immunol., 7: 715-725, 2007). Korean Patent No. KR 10-1027427 discloses trastuzumab (Herceptin, Genentech) variants with increased FcRn binding affinity, and these variants comprise one or more amino acid modifications selected from 257C, 257M, 257L, 257N, 257Y, 279Q, 279Y, 308F and 308Y. Korean Patent Publication No. KR 2010-0099179 provides Bevacizumab (Avastin, Genentech) variants and these variants show an increased half-life in vivo through amino acid modifications comprised in N434S, M252Y/M428L, M252Y/N434S and M428L/N434S. In addition, Hinton et al. also found that T250Q and M428L2 mutants increased the binding to FcRn by 3 and 7 times respectively. Mutating two sites at the same time increased the binding by 28 times. within rhesus monkeys, M428L or T250QM/428L mutants showed a 2-fold increase in plasma half-life (Hinton P R et al., J. Immunol., 176: 346-356, 2006). For more mutation sites comprised in Fc variants with enhanced binding affinity to the neonatal receptor (FcRn), may see in Chinese invention patent CN 201280066663.2. In addition, Studies have conducted T250Q/M428L mutations on the Fc segment of five humanized antibodies not only improved the interaction between Fc and FcRn, but also in the subsequent in vivo pharmacokinetic tests, it was found that the Fc mutant antibody was administered by subcutaneous injection, compared with wild-type antibodies, pharmacokinetic parameters have been improved, such as increased in vivo exposure, decreased clearance, and increased subcutaneous bioavailability (Datta-Mannan A et al., mabs. Taylor & Francis, 4: 267-273, 2012).

Other mutation points that can cause the enhancement of the affinity of the antibody of the present invention to FcRn including but are not limited to the following amino acid modifications: 226, 227, 230, 233, 239, 241, 243, 246, 259, 264, 265, 267, 269, 270, 276, 284, 285, 288, 289, 290, 291, 292, 294, 298, 299, 301, 302, 303, 305, 307, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 382, 383, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 433, 438, 439, 440, 443, 444, 445, 446, wherein the amino acid number in Fc region is the number of the EU index in Kabat.

Fc variants with enhanced binding affinity to FcRn further comprise all other known amino acid modification sites and undiscovered amino acid modification sites.

In optional embodiments, IgG variants may be optimized to have increased or decreased FcRn affinity, as well as increased or decreased human FcγR, including but not limited to FcγRI, FcγRIIa, FcγRIIb, FcγRIIc, FcγRIIIa, and FcγRIIIb affinity including allelic variations thereof.

Preferably, the Fe ligand specificity of IgG variant will determine its therapeutic application. The use of a given IgG variant for therapeutic purposes will depend on the epitope or form of the target antigen, and the disease or indication to be treated. For most targets and indications, enhanced FcRn binding can be more preferred because enhanced FcRn binding may result in a prolonged serum half-life. The longer serum half-life allows for administration with lower frequency and dose during treatment. This characteristic may be particularly preferred when the therapeutic agent is administered in response to indications requiring repeated administration. For some targets and indications, the reduced affinity of FcRN may be particularly preferred when the variant Fc is required to have increased clearance or reduced serum half-life, for example, when the FC polypeptide is used as a developer or radiotherapy agent.

The prolonged half-life Fc change, as described herein "prolonged half-life Fc change" refers to a change in the in vivo half-life of a protein in an Fc polypeptide chain that prolongs a chain that comprises an altered Fc polypeptide as compared to the half-life of a similar Fc protein that comprises the same Fc polypeptide but does not comprise an alteration. The changes can be comprised in the Fc polypeptide chain which is the part of the bispecific antibody. T250Q, M252Y, S254T and T256E were changed (threonine at position 250 is changed to glutamine; methionine at position 252 is changed to tyrosine. Serine at position 254 is changed to threonine. And threonine at position 256 is changed to glutamic acid. Numbered according to EU numberings) are Fc changes that prolong the half-life and can be used in combination, alone or in any combination. These changes and some other changes are described in detail in U.S. Pat. No. 7,083,784. The part of U.S. Pat. No. 7,083,784 describing such change is incorporated herein by reference.

Likewise, M428L and N434S are Fc changes with prolonged half-life and can be used in combination, alone or in any combination. These changes and other changes are described in detail in U.S. Patent Application Publication 2010/0234575 and U.S. Pat. No. 7,670,600. The part of U.S. Patent Application Publication text 2010/0234575 and U.S. Pat. No. 7,670,600 describing such changes are incorporated herein by reference.

In addition, according to the meaning herein, any substitution at one of the following sites can be considered as a half-life prolonging Fc change: 250, 251, 252, 259, 307, 308, 332, 378, 380, 428, 430, 434, 436. Each of these changes, or a combination of these changes, can be used to prolong the half-life of the bispecific antibodies described herein. Other changes that can be used to prolong the half-life are described in detail in international application PCT/US2012/070146, which was filed on 17 Dec. 2012 (publication number: WO 2013/096221). The part of this application describing the foregoing changes is incorporated herein by reference.

Fc changes with prolonged half-life further comprise known technologies and sites that may be discovered in the future and modifications thereof.

The Fc can be derived from any organism including but are not limited to human, mice, rat, rabbit and monkey.

Nucleic acids encoding bispecific antibodies, using the therapeutic agents and antibodies or antibody fragments described herein, those skilled in the art can easily construct multiple clones containing functionally equivalent nucleic acids (e.g., nucleic acids having different sequences but encoding identical effector parts or antibody sequences). Therefore, the present invention provides bispecific antibodies, nucleic acids, nucleic acid variants, derivatives and species homologues encoding antibodies, antibody fragments and conjugates and fusion proteins thereof.

Many nucleic acid sequences encoding immunoglobulin regions comprising VH, VL, hinge, CH1, CH2, CH3, and CH4 regions are known in the art. See, for example, Kabat et al., Sequences of Proteins of Immunological Interest, Public Health Service N.I.H., Bethesda, M D, 1991. According to the teachings provided herein, those skilled in the art can combine the nucleic acid sequences and/or other nucleic acid sequences known in the art to construct nucleic acid sequences encoding bispecific antibodies of the present invention. Exemplary nucleotides encoding the bispecific antibody of the present invention comprise SEQ ID NO: 21.

In addition, based on the amino acid sequences provided herein and elsewhere and the general knowledge in this field, those skilled in the art can determine the nucleic acid sequence encoding the bispecific antibody of the present invention. In addition to the traditional methods of producing cloned DNA fragments encoding specific amino acid sequences, companies such as DNA 2.0 (Menlo Park, CA, USA) and Blue Heron (Bothell, WA, USA) usually adopt chemical synthesis to produce gene-sized DNA in any desired order, thus simplifying the process of producing the DNA.

The method for preparing the bispecific antibody can adopt any method known in the art to prepare the bispecific antibody of the present invention. The early methods of constructing bispecific antibodies are chemical crosslinking method or hybrid hybridoma or tetravalent tumor method (for example, Staerz U D et al., Nature, 314: 628-31, 1985; Milstein C et al., Nature, 305: 537-540, 1983; Karpovsky B et al., J. Exp. Med., 160: 1686-1701, 1984). Chemical coupling method is to connect two different monoclonal antibodies together in a chemical coupling way to prepare bispecific monoclonal antibodies. For example, chemical binding of two different monoclonal antibodies, or for example chemical binding of two antibody fragments, such as two Fab fragments. Hybrid-hybridoma method produces bispecific monoclonal antibodies by cell hybridization or ternary hybridoma, which is obtained by fusion of established hybridomas or fusion of established hybridomas and lymphocytes obtained from mice. Although these technologies are used to manufacture BiAb, various problems have caused such complexes to be difficult to use, such as producing mixed populations containing different combinations of antigen binding sites, difficulties in the aspect of protein expression, needing purity target BiAb, low yield, high production cost, etc.

Recent methods utilize genetically engineered constructs that can produce homogeneous products of a single BiAb without thorough purification to remove unwanted by-products. Such constructs comprise tandem scFv, double antibody, tandem double antibody, double variable domain antibody and heterodimerization using motifs such as Ch1/Ck domain or DNL TM (Chames & Baty, Curr. Opin. Drug. Discov. Devel., 12: 276-83, 2009; Chames & Baty, mAbs, 1: 539-47). Related purification techniques are well known.

The monocytic antibody method can also be used to produce antibodies by cloning and expressing immunoglobulin variable region cDNA produced by single lymphocytes selected for producing specific antibodies, for example, by Babcook J et al., Proc. Natl. Acad. Sci. USA. 93: 7843-7848, 1996; the methods described in WO 92/02551; WO 2004/051268 and WO 2004/106377.

Antigen polypeptides used for producing antibodies such as those used for phage display (or expression on the surface of yeast cells or bacterial cells), for example, for immunizing hosts, can be prepared from genetically engineered host cells containing expression systems by methods well known in the art, or they can be recovered from natural biological sources. For example, nucleic acids encoding one or two polypeptide chains of bispecific antibodies can be introduced into cultured host cells by various known methods (such as transformation, transfection, electroporation, bombardment with nucleic acid-coated particles, etc.). In some implementations, the nucleic acid encoding the bispecific antibody can be inserted into a vector suitable for expression in the host cell before being introduced into the host cell. Typically, the vector may comprise sequence elements that enable the inserted nucleic acid to be expressed at the RNA and protein levels.

The vectors are well known in the art, and many are commercially available. Host cells containing the nucleic acid can be cultured under conditions that enable cells to express the nucleic acid, and the obtained BiAb can be collected from cell populations or culture media. Optionally, BiAb can be produced in vivo, for example, in plant leaves (see, such as., Scheller J et al., Nature Biotechnol., 19: 573-577, 2001 and the references cited therein), in bird eggs (see, such as, Zhu L et al., Nature Biotechnology., 23: 1159-1169, 2005 and references cited therein), or in mammalian milk (see, such as, Laible G et al., Reprod. Fertil. Dev., 25: 315, 2012).

A variety of host cells that can be used comprise, for example, prokaryotic cells, eukaryotic cells, bacterial cells (such as *Escherichia coli* or *Bacillus stearothermophilus*), fungal cells (such as *Saccharomyces cerevisiae* or *Pichia pastoris*), insect cells (such as Lepidoptera insect cells including *Spodoptera fruticosa* cells) or mammalian cells (such as Chinese hamster ovary (CHO) cells, NS0 cells, baby hamster kidney (BHK) cells, monkey kidney cells, Hela cells, human hepatocellular carcinoma cells or 293 cells, etc.).

Bispecific antibodies can be prepared by immunizing suitable subjects (for example, rabbits, goats, mice, or other mammals, including transgenic and rejected foregoing mammals) with immunogenic preparations of bispecific antigens. Suitable immunogenic preparations may be, for example, chemically synthesized or recombinantly expressed bispecific antigens. The preparations may further comprise an adjuvant, for example Freund's complete adjuvant or incomplete adjuvant or similar immunostimulatory compounds. Furthermore, when used to prepare antibodies, especially by the way of in vivo immunization, the bispecific antigens of the present invention can be used alone or preferably as conjugates to vector proteins. such method of enhancing antibody response is well known in the art. According to different antibodies needed, different animal hosts can be used for in vivo immunization. A host that expresses useful endogenous antigens by itself can be used, or a host that has caused defects in useful endogenous antigens can be used.

Bispecific antibodies can be prepared by combining the methods described foregoing.

The bispecific antibody molecule of the present invention can be used as a monoclonal antibody (MAb) for each target. In some implementations, the antibody is chimeric, humanized or fully human.

The monoclonal antibody may be prepared by any method known in the art, such as hybridoma technology (Kohler & Milstein, Nature, 256: 495-497, 1975), trisource hybridoma technology, human B cell hybridoma technology (Kozbor D et al., Immunology Today, 4: 72, 1983) and EBV-hybridoma technique (Cole S P C et al., Monoclonal Antibodies and Cancer Therapy, PP77-96, Alan RLIS, Inc., 1985).

The bispecific antibody or part thereof of the present invention can be used to detect any or all of these antigens (for example, in biological samples, such as serum or plasma) by conventional immunological analysis methods, such as enzyme-linked immunosorbent assay (ELISA), radioimmunoassay (RIA) or histoimmunohistochemistry. The present invention provides a method for detecting an antigen in a biological sample, which comprises: contacting the biological sample with the bispecific antibody or antigen-binding fragment of the present invention which can specifically recognize the antigen, and detecting an antibody or part thereof which binds to an antigen, or a non-binding antibody or part thereof, thereby detecting the antigen in the biological sample. The antibody is directly or indirectly labeled with a detectable substance to facilitate detection of bound or unbound antibodies. Suitable detectable substances comprise various enzymes, repair groups, fluorescent substances, luminescent substances and radioactive substances. Examples of suitable enzymes comprise horseradish peroxidase, alkaline phosphatase, β-galactosidase, acetylcholinesterase; Examples of suitable repair group complexes comprise streptavidin/biotin and avidin/biotin; Examples of suitable fluorescent substances comprise 7-hydroxycoumarin, fluorescein, fluorescein isothiocyanate, rhodamine B, dichlorotriazine amine fluorescein, dansyl chloride or phycoerythrin; Examples of luminescent substances comprise 3-aminophthalic hydrazide; Examples of suitable radioactive substances comprise I125, I131, 5S or 3H.

Pharmaceutical compositions, bispecific antibodies of the present invention or nucleic acids or polynucleotides encoding antibodies of the present application may be used to prepare pharmaceutical compositions or sterile compositions, for example, bispecific antibodies are mixed with pharmaceutically acceptable vectors, excipients or stabilizers. Pharmaceutical compositions can comprise one or a combined (e.g., two or more different) bispecific antibodies of the present invention. For example, the pharmaceutical composition of the present invention may comprise a combination of antibodies or antibody fragments (or immunoconjugates) with complementary activities that bind to different epitopes on the target antigen. Preparations of therapeutic and diagnostic agents can be prepared by mixing with pharmaceutically acceptable vectors, excipients or stabilizers in the form of, for example, lyophilized powder, slurry, aqueous solution or suspension.

The term "pharmaceutically acceptable" refers to when molecular bodies, molecular fragments or compositions are properly administered to animals or humans, they will not produce adverse, allergic or other adverse reactions. Specific examples of some substances that can be used as pharmaceutically acceptable vectors or components thereof comprise sugars (such as lactose), starch, cellulose and derivatives thereof, vegetable oils, gelatin, polyols (such as propylene glycol), alginic acid, etc.

Bispecific antibodies or nucleic acids or polynucleotides encoding antibodies of the present application can be connected to or administered separately from the foregoing pharmaceutically acceptable vectors or some substances of their components (as immune complexes). In the latter case, the bispecific antibody or the nucleic acid or polynucleotide encoding the antibody of the present application can be administered before, after or together with some substances of the foregoing pharmaceutically acceptable vector or its components, or can be administered together with other known therapies (such as anti-cancer therapy, such as radiation).

The composition of the present invention may be in various forms. It comprises, for example, liquid, semisolid and solid dosage forms, for example liquid solutions (e.g., injectable and infusible solutions), dispersant or suspension tablet, pills, powders, liposomes and suppositories. The preferred way depends on the way of administration and the therapeutic use. Typical preferred compositions are injectable or infusible solutions, for example those similar to passive immunization of humans with other antibodies. The route of administration can take many forms, including oral, rectal, transmucosal, enteral, parenteral; intramuscular, subcutaneous, intradermal, intramedullary, intrathecal, intracardiac, intravenous, intraperitoneal, intranasal, intraocular, inhalation, insufflation, topical, dermal, percutaneous or intra-arterial. Preferred administration forms are parenteral (e.g., intravenous, subcutaneous, intraperitoneal, intramuscular). In a preferred implementation, the antibody is administered by intravenous injection or injection. In another preferred implementation, the antibody is injected through intramuscularly or subcutaneously.

The foregoing combination methods, treatment methods and administration methods are well known, and further comprise combinations, treatments and administration methods that may be developed in the future.

The pharmaceutical composition of the present invention can be a combination of two drugs, and can be a combination of products with similar functions and the same functions as those on the market or products with increased therapeutic effects

DESCRIPTION OF THE EMBODIMENTS

Figure 1:
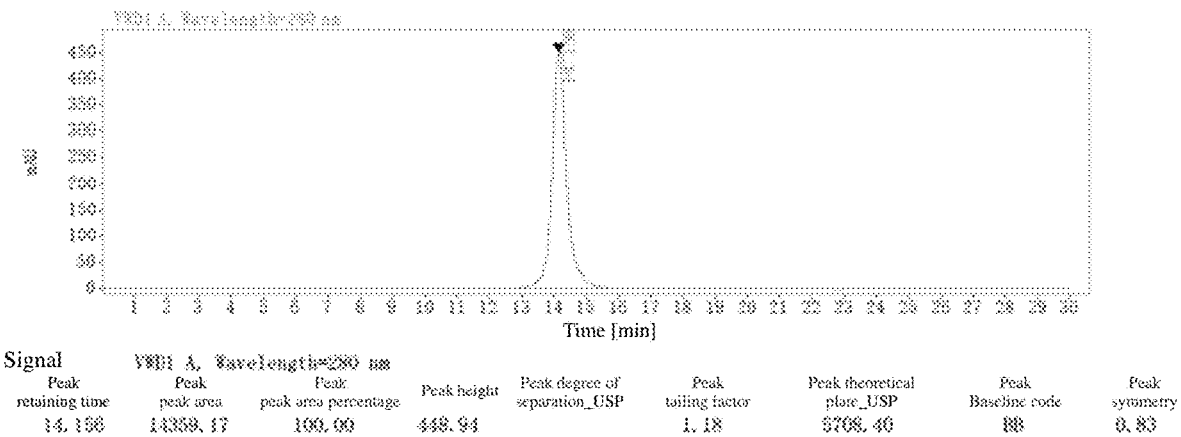
FIG. 1., SEC-HPLC test results of AP163 purified samples.

The present invention is further illustrated by the following embodiments, which should not be construed as further limiting. The contents of all drawings and all references, patents and published patent applications cited in the whole application are hereby expressly incorporated by reference.

In each of the following embodiments, the materials used in the experiment can be purchased or prepared with reference to the existing published technology; Those without marked source and specification are available on the market; various processes and methods not described in detail are conventional methods known in the art.

Embodiment 1, Construction of Bispecific Antibody Molecular Expression Vector

The bispecific antibody AP163 is composed of anti-BCMA scFv, linker peptide L2, anti-CD3 scFv and Fc fragment in series. VH and VL in anti-BCMA scFv and anti-CD3 scFv are connected by linker peptides L1 and L3 respectively. The VH and VL amino acid sequences of scFv against BCMA comprised in AP163 are as shown in SEQ ID NO: 7 and SEQ ID NO: 8, respectively. The VH and VL amino acid sequences of the anti-CD3-scFv comprised in AP163 are as shown in SEQ ID NO: 17 and SEQ ID NO: 18, respectively, and VH and VL are connected by (GGGGS (SEQ ID NO: 22))$_3$. The Fc fragment comprised in AP163 derives from human IgG1, and has several amino acid displacement/substitutions, respectively L234A, L235A, T250Q, N297A, P331S and M428L(EU numbering), meanwhile, K447 at the c-terminal of the Fc fragment is deleted/deleted (EU numbering). Its linker peptide (L2) is composed of flexible peptide and rigid peptide, and the flexible peptide is G2(GGGGS)$_3$ (SEQ ID NO: 29), while the rigid peptide is SSSSKAPPPS (SEQ ID NO: 24). While the composition of linker peptides L1 and L3 in each scFv is (GGGGS (SEQ ID NO: 22))$_3$.

According to the conventional molecular biology method, the coding genes of the foregoing bispecific antibodies are synthesized, and the coding cDNA of the obtained fusion genes are respectively inserted into the corresponding enzyme cutting sites of the eukaryotic expression plasmid pCMAB2M modified by PCDNA3.1. Plasmid pCMAB2M also contains selective markers, so it can have kanamycin resistance in bacteria and can have G418 resistance in mammalian cells. Additionally, when the host cell is DHFR gene expression deficient, the pCMAB2M expression vector contains mice dihydrofolate reductase (DHFR) gene, so that the target gene and DHFR gene can be co-amplified in the presence of methotrexate (MTX) (see U.S. Pat. No. 4,399,216).

Embodiment 2, Expression of Bispecific Antibody Molecules

The expression plasmid constructed foregoing was transfected into mammalian host cell lines to express bispecific antibodies. The host cell line is DHFR enzyme deficient CHO cell (see U.S. Pat. No. 4,818,679), and the host cell in this embodiment selectes CHO-derived cell strain DXB11.

A preferred transfection method is electroporation, but other methods including calcium phosphate co-precipitation and lipofection can also be used. In electroporation, 50 µg expression vector plasmid DNA was added to $5\times10^7$ cells in a cuvette with a Gene Pulser electroporator (Bio-Rad Laboratories, Hercules, CA) set at 300V electric field and 1500 pFd capacitance. Two days after transfection, the culture media was changed into growth medium containing 0.6 mg/mL G418. The subcloned transfectants were diluted to limit, and the secretion rate of each cell line was determined by ELISA. Screening out cell strains expressing bispecific antibodies at high level.

Co-amplification of DHFR gene inhibited by MTX drugs mainly comprises the following steps: co-amplification of transfected fusion protein gene with DHFR gene in growth medium containing increasing concentration of MTX. Limiting dilution of subclones with positive DHFR expression, gradually pressurizing and screening out transfectants which can grow in MTX medium up to 6 µM, determining their secretion rate, screening out cell lines with high expression of foreign proteins. Cell lines with a secretion rate of more than 5 (more preferably about 15) µg/$10^6$ (i.e., one million) were subjected to adaptive suspension culture using serum-free medium. Collecting cell supernatant and separating, purifying bispecific antibody.

Embodiment 3, Purification of Bispecific Antibody

The bispecific antibody AP163 was purified by three-step chromatography. They are affinity chromatography, hydroxyapatite chromatography and anion exchange chromatography (the protein purifier used in this embodiment is AKTA pure 25M of GE company in the United States. The reagents used in this embodiment are all purchased from Sinopharm Chemical Reagents Co., Ltd., and their purity is of analytical grade).

The first step, affinity chromatography: adopt MabSelect Sure affinity chromatography media of GE company (MabSelect Sure, purchased from GE company) or other commercially available affinity media (for example Diamond protein A of Bergeron company, etc.) for sample capture, concentration and partial pollutant removal. Firstly, the equilibrium buffer(20 mM PB, 140 mM NaCl, pH 7.4) is used to balance 3-5 column volumes (CV) of the chromatographic column at a linear flow rate of 100-200 cm/h; sample the clarified fermentation broth at a linear flow rate of 100-200 cm/h, and the load is not more than 20 mg/m; After loading the sample, balance 3-5 column volumes (CV) of chromatographic column with balance buffer(20 mM PB, 140 mM NaCl, pH 7.4) at a linear flow rate of 100-200 cm/h to wash unbound components; use decontamination buffer 1(50 mM NaAc-HAc, 1 M NaCl, pH 5.0) to wash 3-5 column volumes of chromatographic column at a linear flow rate of 100-200 cm/h to remove some pollutants; use decontamination buffer 2(50 mM NaAc-HAc, pH 5.0) to balance 3-5 column volumes (cv) of the chromatographic column at a linear flow rate of 100-200 cm/h; then eluting the target product with elution buffer(40 mM NaAc-HAc, pH 3.5) at a linear flow rate not higher than 100 cm/h, and collecting the target peak.

The second step, hydroxyapatite chromatography: using CHT TypeII of BIO-RAD company or other commercially available hydroxyapatite media (CHT TypeII, purchased from BIO-RAD company) for intermediate purification to reduce polymer content. After the target protein is polymerized, there are differences in properties between polymer and monomer, including charge characteristics as well as calcium ion chelation. We use the difference in charge characteristics to separate the both. At first, the equilibrium buffer(20 mM PB, pH 7.0) is used to balance 3-5 column volumes (CV) of the chromatographic column at a linear flow rate of 100-200 cm/h; the target protein obtained by affinity chromatography in the first step is adjusted to pH 7.0, then loaded with the sample, the load was controlled less than 5 mg/ml; after loading the sample, wash the chromatographic column for 3-5 column volumes (CV) at a linear flow rate of 100-200 cm/h with a balance buffer (20 mM PB, pH 7.0); at last, the target protein was eluted with an elution buffer(20 mM PB, 1M NaCL, pH 7.0) at a gradient of 0-50% and 10 column volumes (CV) at a linear flow rate not higher than 100 cm/h, the eluted components were collected in sections and sent to SEC-HPLC. Combining target components with monomer percentage greater than 95% for next chromatography.

The third step, using anion exchange chromatography: Q-HP of Bergeron company or other commercially available anion exchange chromatography media (Q-HP, purchased from Bergeron company) (for example, Q HP of GE, Toyopearl GigaCap Q-650 of TOSOH, DEAE Beads 6FF of Tiandi Renhe, Generik MC-Q of Sepax technology, Fractogel EMD TMAE of Merck, Q Ceramic HyperD F of Pall) for fine purification to further remove pollutants (HCP and DNA, etc.). firstly, washing the chromatographic column by using an equilibrium buffer(20 mM PB, 0.15M NaCL, pH 7.0) at a linear flow rate of 100-200 cm/h for 3-5 column volumes (cv); sample the target protein separated by hydroxyapatite chromatography in the second step, collect and flow through, after loaded with sample, and wash the chromatographic column for 3-5 column volumes (CV) with equilibrium buffer(20 mM PB, 0.15M NaCL, pH 7.0) at a linear flow rate of 100-200 cm/h; collect the components of the permeation, and send samples for protein content, SEC-HPLC and electrophoresis detection.

Figure 2:
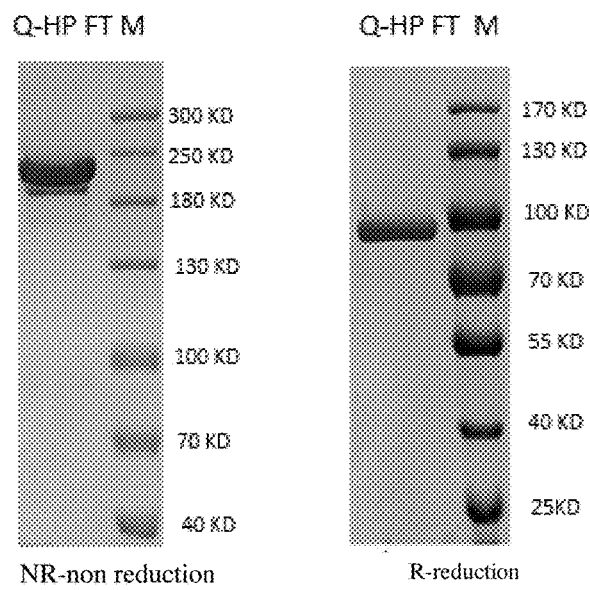
FIG. 2., SDS-PAGE electrophoresis results of AP163 purified samples.

SEC-HPLC purity results and SDS-PAGE electrophoresis results of the samples are shown in FIG. 1 and FIG. 2 respectively, in which SEC-HPLC results show that the purity of the main peak of bispecific antibody after three-step chromatography is over 95%, and the SDS-PAGE electrophoresis band pattern is in line with expectations. after non-reduction electrophoresis (180 KDa), a clear (90 KDa) single chain band can be obtained after reduction.

Embodiment 4, Biological Function Evaluation of Anti-BCMAxCD3 Bispecific Antibody In Vitro (1) Binding Activity of Bispecific Antibody to BCMA Positive Cells and T Cells Human myeloma NCI-H929 cells, human Jurkat-LUC cells, human T-lymphocyte leukemia HUT-78 cells, human myeloma MM.1S cells, human promyelocytic leukemia HL60 cells, human T cells and cynomolgus monkey T cells were cultured, the cells were collected by centrifugation and resuspended with 1% DPBS (Duchenne Phosphate Buffer), and the cell densities were adjusted to $2\times10^6$ cells/ml respectively, place in 96-well plates, 100 µl per well. The bispecific antibody AP163 to be tested was diluted by gradient, 100 µl per well, incubated in 5% $CO_2$ incubator at 37° C. for 1 hour. Centrifuge, add 200 µl 1% DPBS to each well, wash for 2 times, centrifuge to remove supernatant, add 100 µl fluorescent secondary antibody (Alexa Fluor® 647 goat anti-human IgG(H+L) antibody) to each well, incubate for 1 h in 5% $CO_2$ incubator at 37° C. Centrifuge to remove supernatant, wash the plate twice with 1% DPBS, add 100 μl 1% DPBS to each well for resuspension, and detect the signal intensity by flow cytometry. With the average fluorescence intensity as the y axis and antibody concentration as the x axis, the binding activity of AP163 with BCMA+ cells and CD3+ cells was calculated by using a software GraphPad Prism 6.

Figure 3:
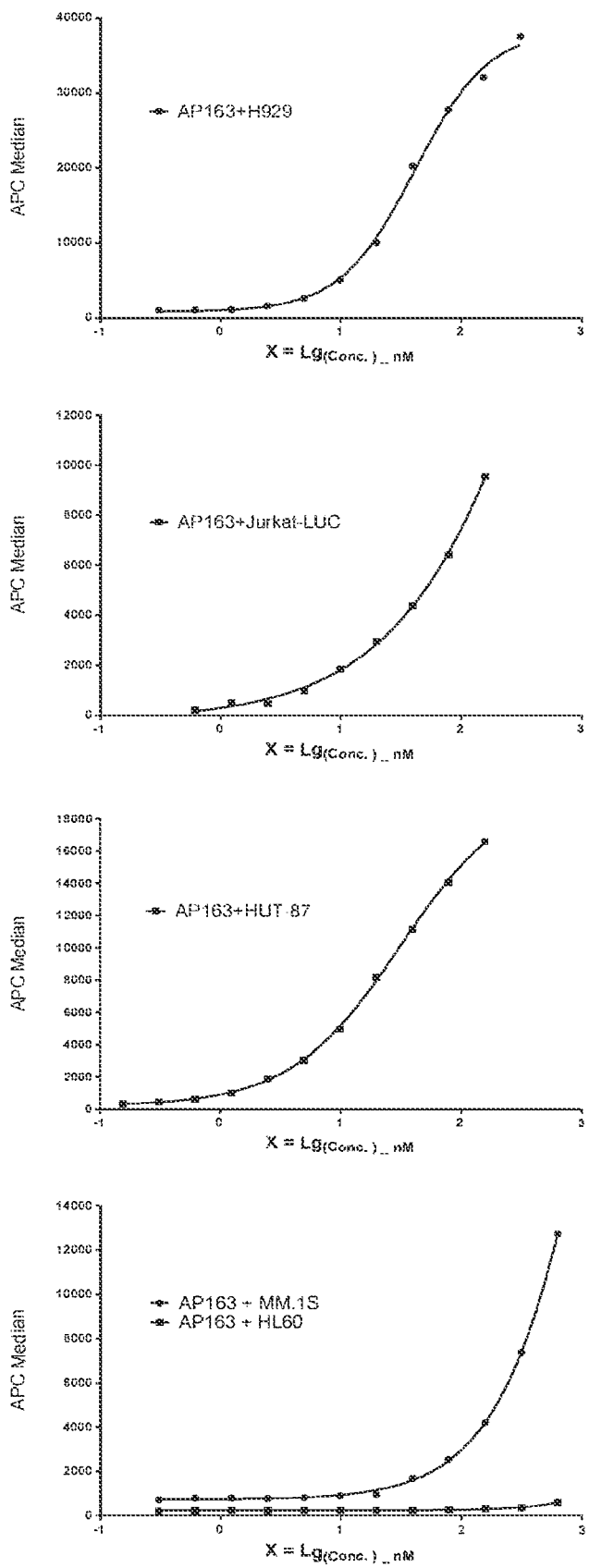
FIG. 3., determination of binding ability of bispecific antibody to BCMA positive cells.
Figure 4:
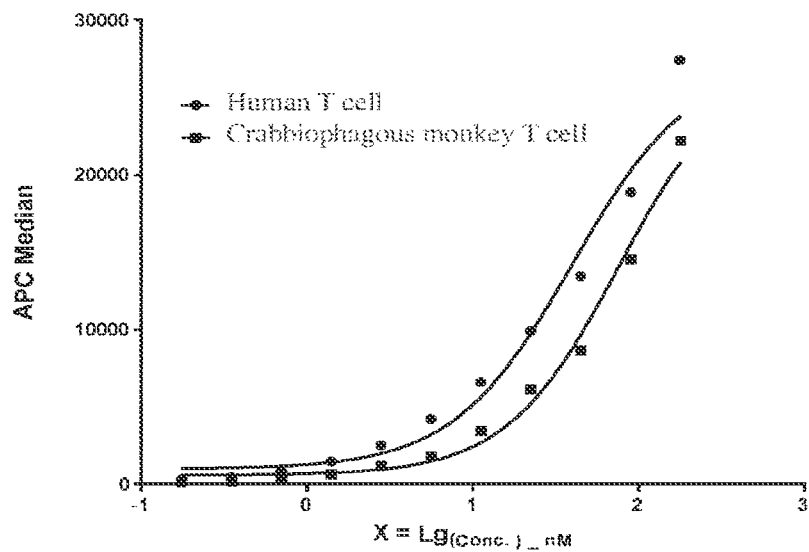
FIG. 4., determination of binding ability of bispecific antibody to different T cells.

As shown in FIG. 3, FIG. 4, at the cell level, AP163 can specifically bind to BCMA positive cells and have dose-effect relationship; at the same time, AP163 can highly specifically bind to human T cells and cynomolgus monkey T cells, and have dose-effect relationship.

(2) Determination of Binding Ability and Cross-Reactivity of Bispecific Antibodies to CD3 and BCMA Proteins of Human Monkey Species CD3 and BCMA of human and monkey coated with antigen were diluted to 0.1 μg/ml with PBS, added into 96-well plate, coated at 2-8° C. overnight. The liquid in the plate was discarded, PBST containing skimmed milk powder was added to seal it at room temperature for 2 h, PBST washed the plate twice. The bispecific antibody to be tested was diluted 4 times, with 12 gradients, 2 wells per concentration, 100 μl/well added to the 96-well plate, and incubated at room temperature for 2 hours. Unbound bispecific antibody was washed away with PBST, biotinylated human BCMA protein or human CD3 protein was diluted to 0.1 μg/ml, and HRP-labeled streptavidin (BD, Item No. 554066) was mixed in 1:1000, and added to 96-well plate, 100 μl/well, incubated for 1 h at room temperature. Thereafter, the 96-well plate was washed with PBST, TMB was added, 100 μl/well, the color was developed at room temperature in the dark for 2-3 min, then 1 M HCL was added to stop the color reaction. The absorbance of OD450 nm was detected by microplate reader. Using logarithmic value of sample concentration as abscissa and absorbance value as ordinate, a four-parameter nonlinear regression and a variable slope equation were made. The $EC_{50}$ value of binding of bispecific antibody to antigen was calculated. The experimental results are shown in Table 1, the $EC_{50}$ value of bispecific antibody binding to human CD3 and BCMA protein and cynomolgus monkey CD3 and BCMA protein is very small, the binding ability of bispecific antibody to different species antigens is basically the same.

TABLE 1 determination result of the binding ability and cross reactivity of bispecific antibody to human monkey species CD3 and BCMA proteins

| | | AP163 concentration (μg/ml) | | | | |
|---|---|---|---|---|---|---|
| | | 0.001 | 0.01 | 0.015 | 0.1 | 0.15 |
| $EC_{50}$ | humanCD3 | 0.1 | 0.12 | 0.75 | 1.3 | 1.6 |
| | monkeyCD3 | 0.1 | 0.12 | 0.75 | 1.3 | 1.6 |
| | humanBCMA | 0.1 | 0.12 | 0.25 | 0.6 | 1.25 |
| | monkeyBCMA | 0.1 | 0.12 | 0.25 | 0.7 | 1.25 |

(3) Determination of the Ability of Bispecific Antibody to Bind Target Cells and Effector Cells at the Same Time.

Figure 5:
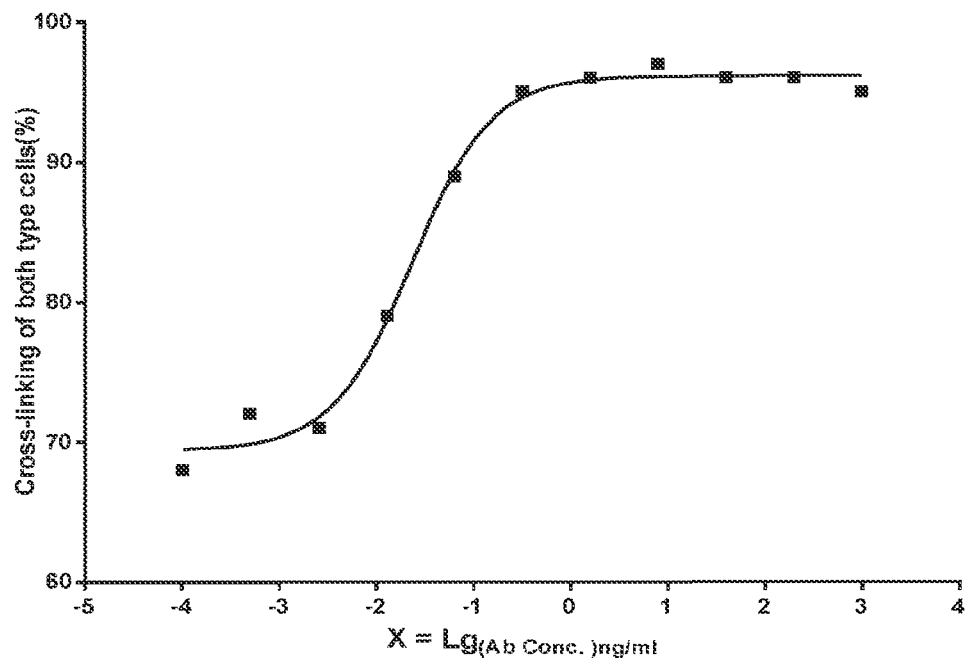
FIG. 5., determination of ability of bispecific antibody to bind target cells and effector cells simultaneously.

Normal cultured human myeloma NCI-H929 cells were used as target cells, which were stained and labeled with PKH26 staining reagent, the cells were resuspended with 1640 complete culture media, the cell density was adjusted to $1\times10^5$ cells/ml, and 50 μl/well was added into 96-well cell culture plate. The bispecific antibody was diluted with culture medium gradient, added at 50 μl/well. Add effector cells (amplify cultured T cells) 5 times as many as target cells, 50 μl/well. Incubate in 5% $CO_2$ incubator at 37° C. for 1 h, so that the sample to be tested and cells are fully mixed and bridge reaction occurs. Wash the 96-well plate with DPBS, detect it by flow cytometry, and capture T cells, then T cells with PKH26 signal are bridged cells, calculate the bridging ratio by statistical data. It can be seen from FIG. 5 that AP163 can specifically induce bridging reaction between tumor cells and target cells, and has a dose-effect relationship.

(4) Activation of CD4+T Cells/CD8+T Cells Mediated by Bispecific Antibodies

Three healthy voluntary blood donors were recruited, peripheral blood was extracted and PBMC was extracted, CD4+T cells and CD8+T cells in PBMC were separated and enriched by CD4+T cell separation kit and CD8+T cell separation kit, the cells were suspended in 1640 complete culture medium containing 10% FBS, and the cell density was adjusted to $1\times10^6$ cells/ml, and added to 96-well cell culture plate with 50 μl/well. Human myeloma NCI-H929 cells were cultured, the cell density was adjusted to $1\times10^5$ cells/ml, 50 μl was added to each well. The bispecific antibody was diluted by gradient, and was added into 96-well plate at 50 μl/well, and incubated in incubator at 37° C. for 24 hours. The supernatant was centrifuged, and the release of granzyme in the supernatant was detected by ELISA. The $EC_{50}$ of CD4+T cell/CD8+T cell activation mediated by bispecific antibody was calculated by GraphPad Prism 6.

Figure 6:
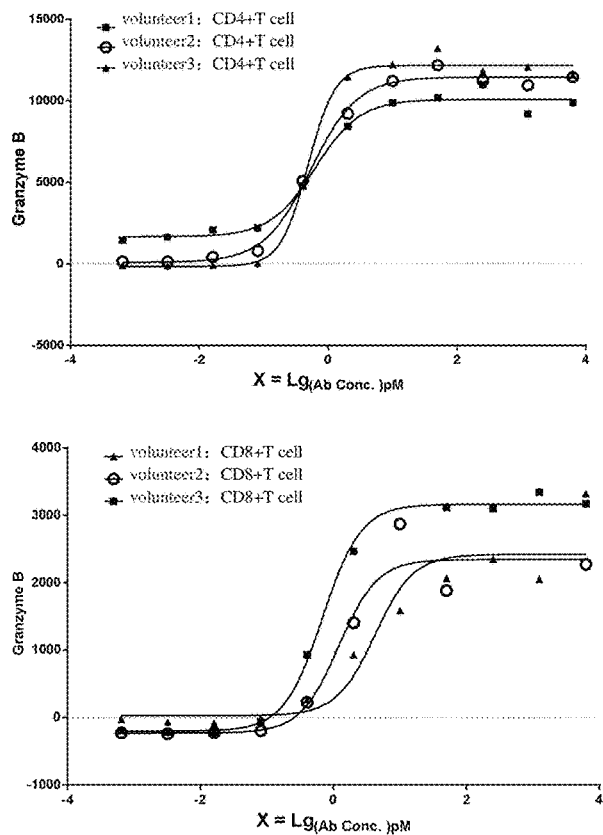
FIG. 6., activation of CD4+T cells/CD8+T cells mediated by bispecific antibodies.

As shown in FIG. 6 and table 2, AP163 can mediate the release of granzyme when CD4+T cells and CD8+T cells of three healthy volunteers kill tumor cells, with a dose-effect relationship.

TABLE 2

$EC_{50}$ of releasing granzyme by activating CD4+T cells/CD8+T cells mediated by bispecific antibody

| Volunteer No. | CD4+T cells (pM) | CD8+T cells (pM) |
|---|---|---|
| 1 | 0.6275 | 4.204 |
| 2 | 0.5341 | 1.202 |
| 3 | 0.4826 | 0.6863 |

(5) Evaluation of the Ability of Bispecific Antibody to Activate T Cells

Jurkat T cells containing NFAT RE reporter gene (purchased from BPS Bioscience) can overexpress luciferase in the presence of bispecific antibody and BCMA positive cells, the activation degree of Jurkat T cells can be quantified by detecting the activity of luciferase. In particularly, H929 cells were centrifuged and resuspended, the cell density was adjusted to $2\times10^5$ cells/ml, and 40 μl/well was added into a 96-well cell culture plate. The NFAT-Jurkat cell density was adjusted to $2\times10^6$ cells/ml, and 40 μl was added to each well. The bispecific antibody AP163 was diluted to 50 μg/mL with culture medium, after 10 times dilution, 20 μl was added to each well, and incubated in 5% $CO_2$ incubator at 37° C. for 48 hours. After washing the plate, 100 μl/well of Steady-Glo® Luciferase was added respectively, and after 5 minutes of reaction, the cold luminescence value was detected by enzyme-labeled instrument. With the concentration of bispecific antibody as the x-axis and the intensity of fluorescein as the y-axis, the $EC_{50}$ of T cells activated by bispecific antibody was calculated by the software GraphPad Prism 6.

Figure 7:
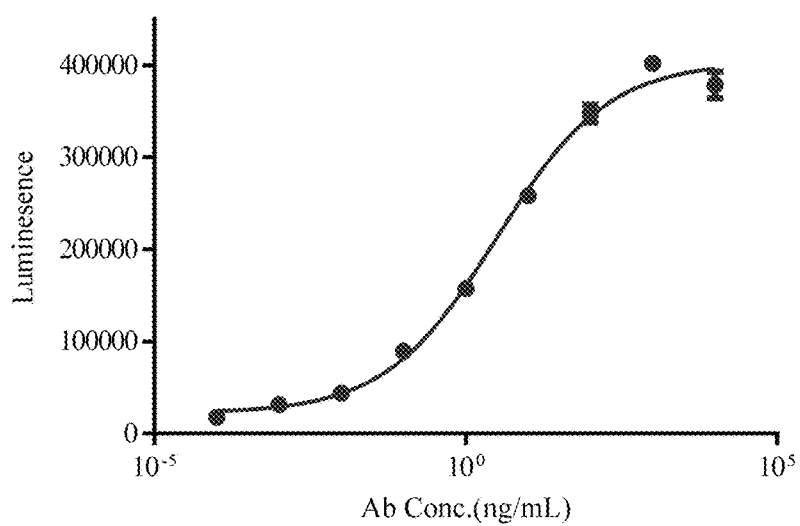
FIG. 7., determination of ability of bispecific antibody to activate Jurkat T cells of reporter gene cell strains.

As shown in FIG. 7, AP163 can specifically activate NFAT-Jurkat cells with $EC_{50}$ value of 3.161 ng/ml, and its concentration is proportional to the signal intensity.

(6) the Ability of T Cells to Kill Tumor Cells Mediated by Bispecific Antibodies T cells of human and cynomolgus monkeys were cultured, the cell density was adjusted to $10^6$ cells/ml, and 50 μl/well were added into 96-well cell culture plates respectively. Normal cultured human myeloma NCI-H929 cells were used as target cells, and the cell density was adjusted to $1\times10^5$ cells/ml, and 50 μl/well was added. Then, 50 μl of gradient diluted bispecific antibody AP163 was added to each well, and was incubated for 24 h in 5% $CO_2$ incubator at 37° C. Add 40 μl Bright-Glo reagent to each well, and let it stand for 3 min at room temperature in the dark. the RLU value was detected by multi-functional microplate reader, and analyzed by software GraphPad Prism 6, and the $EC_{50}$ value of killing H929 cells mediated by bispecific antibody was calculated.

Figure 8:
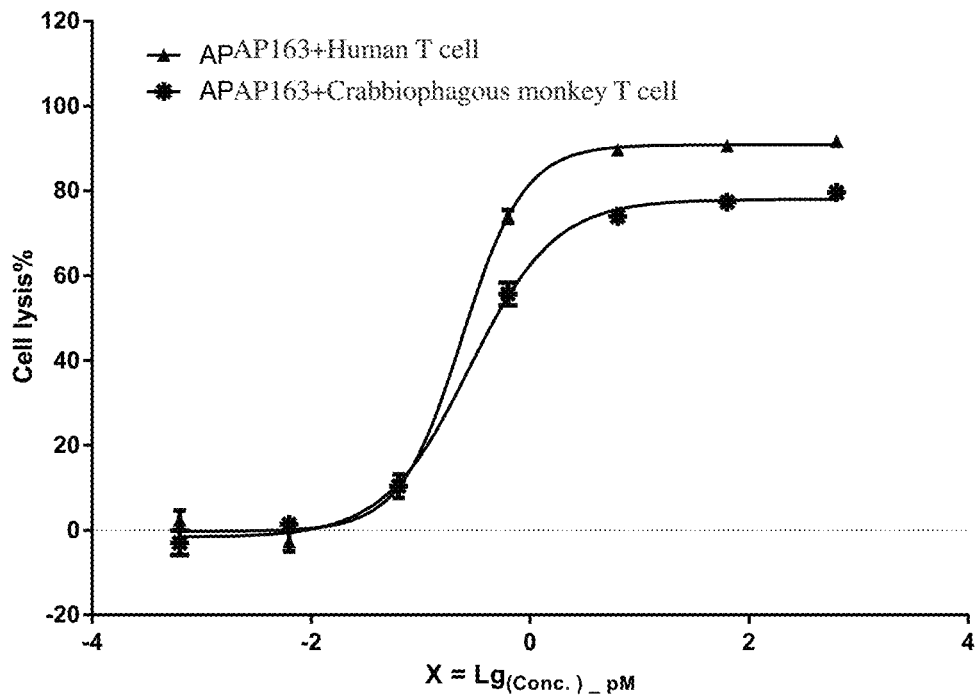
FIG. 8., determination of ability of bispecific antibody-mediated T cells to kill tumor cells.

As shown in FIG. 8, the $EC_{50}$ value of AP163 mediated human t cells killing tumor cells was 0.239 μM, and that of cynomolgus monkey t cells killing tumor cells was 0.278 μM. AP163 can specifically mediate T cells of human and cynomolgus monkeys to kill tumor cells, and H929 cells with high expression of BCMA showed significant killing effect, with a dose-effect relationship.

(7) Evaluation of Cytokine Release Caused by Bispecific Antibody

To evaluate the ability of bispecific antibody to activate T cells alone or depending on target cells to cause cytokine release.

Primary T cells were cultured, centrifuged, collected and resuspended with 1% PBSB, the cell density was adjusted to $1\times10^6$ cells/ml, respectively, and placed in a 96-well plate with 90 μl/well. The maternal monoclonal antibody AB314 (refer to WO2007042261 patent document for details) and bispecific antibody AP163, which recognize CD3, are diluted to 10000 ng/mL with culture medium respectively. after 10 times gradient dilution, 10 μl/well is added to 96-well plate, and then cultured in 37° C., 5% $CO_2$ incubator. After incubation for 24 h and 48 h, the supernatants were collected and analyzed by LEGENDplex™ human Th1/Th2 kit, and the signal intensity was detected by flow cytometry. With cytokine concentration as y-axis and antibody concentration as x-axis, the release of cytokines from activated t cells by AB314 and AP163 was calculated by using GraphPad Prism 6. The results showed that in the absence of target cells, AB314 activated primary T cells for 24 hours, which caused the release of cytokines IL-4, IL-5 and TNF-α; however, AP163 activated primary T cells, and there was no significant cytokine release in 24 h and 48 h.

Human T cells were cultured, centrifuged and collected, and suspended in 1640 complete culture medium of 10% FBS, the cell density was adjusted to $1\times10^6$ cells/ml, and placed in a 96-well plate with 50 μl/well. The cell density of human myeloma NCI-H929 was adjusted to $1\times10^5$ cells/ml, and 50 μl/well was added. After gradient dilution, AP163 was added into 96-well plate at 37° C. in 5% $CO_2$ incubator for 1,2,3,4,5,6,24 h respectively. After incubation, 50 μl supernatant was taken from each well, and the release of 8 cytokines in the supernatant was detected by 8 cytokine detection kit. The experimental results show that AP163 can activate T cells to release IL-5, IL-13, IL-2, IL-6, IL-10, IFN-γ, TNF-α and IL-4 in a time-dependent manner, as shown in table 3.

TABLE 3

| | release of cytokines caused by bispecific antibodies | | | | | | | |
|---|---|---|---|---|---|---|---|---|
| time | IL-5 (pg/ml) | IL-13 (pg/ml) | IL-2 (pg/ml) | IL-6 (pg/ml) | IL-10 (pg/ml) | IFN-γ (pg/ml) | TNF-α (pg/ml) | IL-4 (pg/ml) |
| 1 h | <1.95 | <1.82 | <2.19 | <0.43 | <2.07 | <52.52 | <1.82 | <1.95 |
| 2 h | <1.95 | <1.82 | <2.19 | <0.43 | <2.07 | <52.52 | <1.82 | <1.95 |
| 3 h | <1.95 | 8.73 | <2.19 | <0.43 | <2.07 | 365.35 | 124.72 | <1.95 |
| 4 h | <1.95 | 17.83 | 4.73 | <0.43 | <2.07 | 678.89 | 201.7 | <1.95 |
| 5 h | <1.95 | 16.05 | 4.83 | <0.43 | <2.07 | 646.17 | 210.06 | <1.95 |
| 6 h | <1.95 | 34.98 | 6.42 | <0.43 | <2.07 | 1203.93 | 263.52 | <1.95 |
| 24 h | 100.71 | 89.98 | <2.19 | <0.43 | 3.98 | >1706.27 | 203.47 | 4.81 |

(8) T Cells Mediated by Bispecific Antibodies Kill BCMA-Positive Human Tumor Cells Under Different Effective Target Ratios To culture human T cells, the cell densities were adjusted to $2\times10^7$ cells/ml, $1\times10^7$ cells/ml, $1\times10^6$ cells/ml, $1\times10^5$ cells/ml, $1\times10^4$ cells/ml and $1\times10^3$ cells/ml, and 50 μl per well was added to 96-well cell culture plates. Human myeloma NCI-H929 cells were used as target cells, and the cell density was adjusted to $1\times10^5$ cells/ml, and 50 μl/well was added. Then, 50 μl of gradient diluted AP163 was added to each well, and was incubated for 24 h in 5% $CO_2$ incubator at 37° C. Add 40 μl Bright-Glo reagent to each well, and let it stand for 3 min at room temperature in the dark. the RLU value was detected by multi-functional microplate reader, and analyzed by software GraphPad Prism 6, and the $EC_{50}$ value of killing H929 cells mediated by bispecific antibody was calculated.

Figure 9:
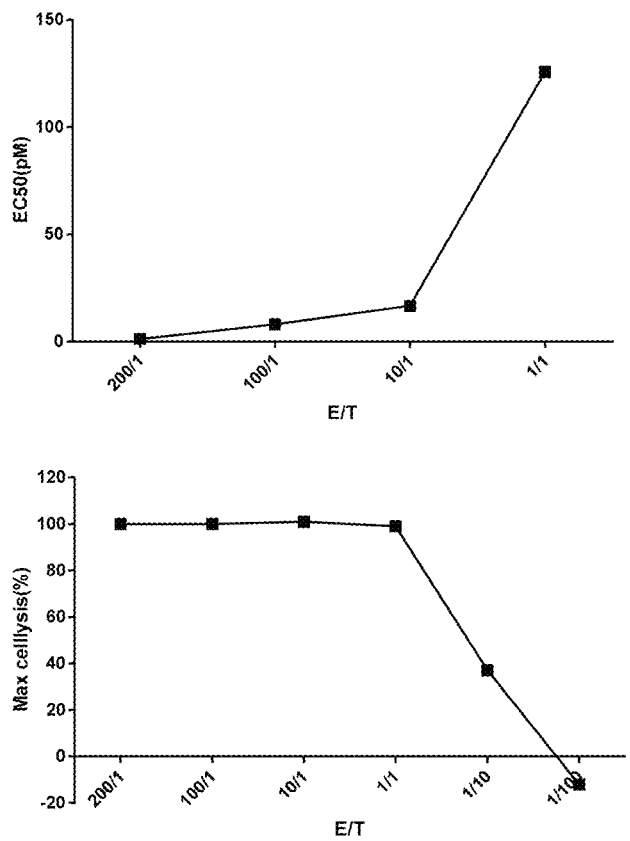
FIG. 9., determination of ability of bispecific antibody-mediated T cells to kill BCMA positive cells under different ratio of effect to target.

As shown in FIG. 9, when ratio of effect to target (E/T) is higher than 1/1, the efficiency of AP163-mediated T cell killing tumor cells can reach 100% killing; when E/T is lower than 1/1, $EC_{50}$ value gradually increases with the decrease of E/T.

(9) to Evaluate the Effects of Dexamethasone and Indomethacin on AP163-Mediated PBMC Killing Tumor Cells Twelve healthy voluntary blood donors were recruited, peripheral blood was extracted and PBMC was extracted, the cells were suspended in 1640 complete culture medium containing 10% FBS, and the cell density was adjusted to $3\times10^6$ cells/ml. 50 μl per well was added to the 96-well cell culture plate. Diluents of dexamethasone and indomethacin were prepared, and 50 μl per well was added to the 96-well plate to incubate PBMC for 1 h and 14 h, respectively; the control group was added with the same volume of buffer. The adjusted cell density of human myeloma NCI-H929 cells was $1\times10^5$ cells/ml, with 50 μl per well. Then, 50 μl of gradient diluted AP163 was added to each well, and incubated in 5% $CO_2$ incubator at 37° C. for 4, 8, 12, 24, 48 h respectively, 40μ L of Bright-GLO reagent was added to each well, and left standing at room temperature for 3 min in the dark, the RLU value was detected by multi-functional microplate reader. The analysis of data showed that the incubation of PBMC with dexamethasone or indomethacin had little effect on AP163-mediated PBMC killing tumor cells.

Embodiment 5 Pharmacodynamic Study of Anti-BCMAxCD3 Bispecific Antibody in Mice Transplanted Tumor Model (1) NPG Mice were Subcutaneously Inoculated with Human CIK Cells and Human Myeloma Cells NCI-H929 to Make a Transplanted Tumor Model.

Human myeloma NCI-H929 cells and CIK cells (induced by activation of human PBMC to the 10th day) were inoculated subcutaneously in the right anterior flank of female NPG mice in different proportions. One hour after inoculation, mice were randomly divided into 4 groups, with 4 mices in each group. The administration was started on the day of grouping, and all groups were given intraperitoneal injection, while the control group was given PBS solution with the same volume, and the dose of AP163 was 0.2 mg/kg. It was administered twice a week for 4 weeks. The tumor volume and weight were measured once every three days, and the weight and tumor volume of mice were recorded. At the end of the experiment, the animals were euthanized, and the tumors were stripped, weighed and photographed, and the relative tumor inhibition rate (TGI %) was calculated.

As shown in Table 4, at the end of the experiment, the average tumor volume of 1/1 control group and ½ control group was $1501\pm351$ mm³ and $1555\pm244$ mm³; respectively, the mean tumor volume and TGI % of 1/1 AP163 experimental group were $99\pm38$ mm³ and 93%, respectively. the mean tumor volume and TGI % of 1/1 AP163 experimental group were $481\pm215$ mm³ and 70.2%. The foregoing results indicated that AP163 has an obvious tumor-inhibiting effect, and at the same time, AP163 is safe and has no obvious toxic effects on experimental animals.

TABLE 4

| Pharmacodynamic effect of AP163 on NCI-H929 NPG mouse model | | | | | | |
|---|---|---|---|---|---|---|
| CIK/NCI-H929 groups | | dose (mg/kg) | administration mode | tumor volume (mm³) | tumor weight (g) | tumor inhibition rate (%) |
| 1/1 | PBS | — | i.p.biw | 1501 ± 351 | 2.34 ± 0.46 | — |
| 1/1 | AP163 | 0.2 | i.p.biw | 99 ± 38 | 0.17 ± 0.06 | 93 |
| 1/2 | PBS | — | i.p.biw | 1555 ± 244 | 2.32 ± 0.28 | — |
| 1/2 | AP163 | 0.2 | i.p.biw | 481 ± 215 | 0.69 ± 0.37 | 70.2 |

Note:

i.p: intraperitoneal injection, biw: twice a week (2) NPG Mice were Subcutaneously Inoculated with Human CIK Cells and Human Burkkit's Lymphoma Raji Cells to Make a Transplanted Tumor Model.

Raji cells of human Burkkit's lymphoma were mixed with CIK after culture and amplification (the proportion of Raji cells to CIK cells was 1:1), and mixed with Matrigel in a volume proportion of 1:1 and inoculated subcutaneously on the right back of female NPG mice. One hour after inoculation, mice were randomly divided into 4 groups according to their body weight. On the same day of grouping, the control group was administrated the same volume of PBS solution, the administration doses of the experimental group of AP163 was 1 mg/kg, 0.1 mg/kg and 0.01 mg/kg respectively. All groups were administrated intraperitoneal injection twice a week for 3 weeks. The tumor volume and weight were measured once every three days, and the weight and tumor volume of mice were recorded. At the end of the experiment, the animals were euthanized, and the tumors were stripped, weighed and photographed, and the relative tumor inhibition rate (TGI %) was calculated.

The results are seen in Table 5, at the end of the experiment, the average tumor volume of the control group was 1750±653 mm$^3$; the mean tumor volume of AP163 1 mg/kg, 0.1 mg/kg and 0.01 mg/kg test group was 0.00±0.00 mm$^3$, which were significantly different from that of solvent control group (P<0.05), the TGI of the three groups was 100%, which indicated that the bispecific antibody AP163 had extremely significant anti-tumor effect.

average tumor volume of the control group was 1647.79±247.90 mm$^3$; the mean tumor volume of AP163 1 mg/kg test group was 0.00±0.00 mm$^3$, and TGI % was 100%, the mean tumor volume of AP163 0.1 mg/kg test group was 8.00±5.24 mm$^3$, and TGI % was 99.51%. The experimental results show that the antibody AP163 has a very significant anti-tumor effect. Under the experimental conditions, AP163 significantly inhibited the growth of tumor at all concentrations, and AP163 also showed good safety, without obvious toxic effects on experimental animals.

(4) NPG Mice were Subcutaneously Inoculated with Human CIK Cells and Human Burkkit's Lymphoma Daudi Cells to Make a Transplanted Tumor Model.

Daudi cells of human Burkkit's lymphoma were mixed with CIK (the density of Daudi cells is 5×10$^6$ cells/ml, the density of CIK cells is 1×10$^6$ cells/ml) and Matrigel in a volume ratio of 1:1, and inoculated subcutaneously on the right back of female NPG mice. One hour after inoculation, mice were randomly divided into 6 groups according to their body weight. On the same day of grouping, the control group was administrated the same volume of PBS solution, the administration doses of the experimental group of AP163 was 1 mg/kg, 0.2 mg/kg and 0.04 mg/kg respectively. All groups were administrated intraperitoneal injection once every two days for 8 times, and the experiment ended 10 days after the last administration. The tumor volume and weight were measured twice every week, and the weight and

TABLE 5

Pharmacodynamic effect of AP163 on Raji NPG mice model

| groups | administration | dose (mg/kg) | administration mode | tumor volume (mm$^3$) | tumor weight (g) | tumor inhibition rate (%) |
|---|---|---|---|---|---|---|
| Control group | PBS | — | i.p.biw*6 | 1750 ± 653 | 2.158 ± 0.945 | — |
| L | AP163 | 0.01 | i.p.biw*6 | 0 | 0 | 100 |
| M | AP163 | 0.1 | i.p.biw*6 | 0 | 0 | 100 |
| H | AP163 | 1 | i.p.biw*6 | 0 | 0 | 100 |

Note:
i.p: intraperitoneal injection,
biw: twice a week (3) NPG Mice were Subcutaneously Inoculated with Human CIK Cells and Human Myeloma Cells RPMI-8226

Human myeloma cells RPMI-8226 and CIK were inoculated subcutaneously on the right back of female NPG mice, after inoculation for 1 hour, they were randomly divided according to the weight of mice, and the drug was administered on the same day. There are 7 rats in the first group and 8 rats in the rest of the two groups. On the same day of grouping, the control group was given the same volume of PBS solution, and the dose of AP163 experimental group was 1 mg/kg and 0.1 mg/kg, respectively. All groups were administrated an intraperitoneal injection once every two days for 8 consecutive times, and the experiment ended 18 days after the last administration. The tumor volume and weight were measured twice every week, and the weight and tumor volume of mice were recorded. At the end of the experiment, the animals were euthanized, and the tumors were stripped, weighed and photographed, and the relative tumor inhibition rate (TGI %) was calculated.

Figure 10:
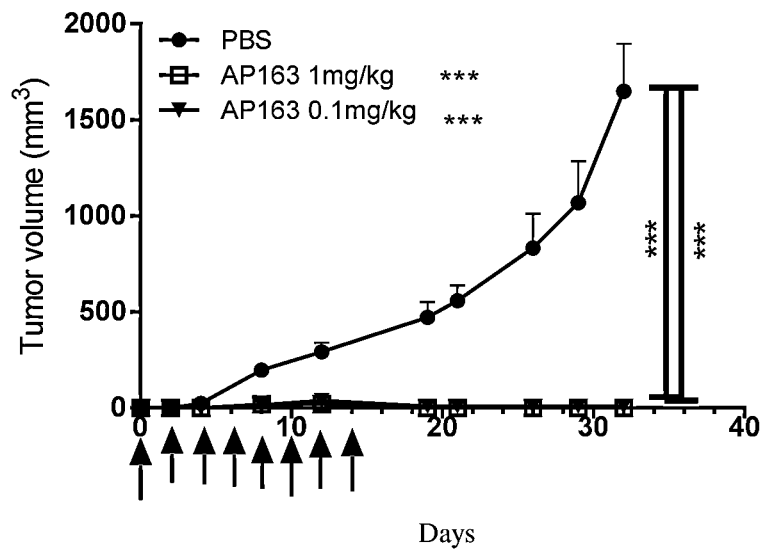
FIG. 10., in vivo anti-tumor effect of bispecific antibody in the transplanted tumor model of subcutaneous co-inoculation of human CIK cells and human myeloma cells RPMI-8226 in NPG mice. Note: The arrow represents the time of each administration; *** indicates that there are significant differences.

As shown in FIG. 10, at the end of the experiment (32 days after the first administration), the weight of animals in each group increased, and there was no significant difference in the weight of animals in different groups (P>0.05). The tumor volume of mice were recorded. At the end of the experiment, the animals were euthanized, and the tumors were stripped, weighed and photographed, and the relative tumor inhibition rate (TGI %) was calculated.

Figure 11:
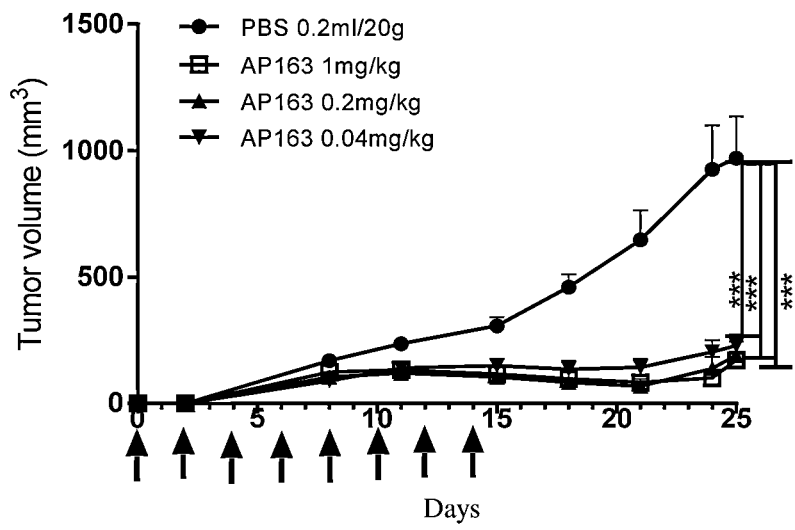
FIG. 11., in vivo anti-tumor effect of bispecific antibody in the transplanted tumor model of subcutaneous co-inoculation of human CIK cells and human Burkkit's lymphoma Daudi cells in NPG mice. Note: The arrow represents the time of each administration; * * * indicates that there are significant differences.

The results are shown in FIG. 11. at the end of the experiment (25 days after the first administration), the weight of animals in each group increased, with no significant difference compared with the control group (P>0.05). At the end of the experiment, the average tumor volume of the control group was 970.83±165.40 mm$^3$; the mean tumor volumes of AP163 1 mg/kg, 0.2 mg/kg and 0.04 mg/kg groups were 171.99±32.60 mm$^3$, 190.82±53.60 mm$^3$ and 228.68±44.96 mm$^3$ respectively, and the corresponding TGI % were 82.28%, 80.34% and 76.44% respectively, and compared with the control group, the anti-tumor effects were significantly different (P<0.05), which indicated that AP163 could significantly inhibit the growth of tumor at all drug concentrations, and it was safe and had no obvious toxic effect on experimental animals.

Embodiment 6 Safety Evaluation Test of Anti-BCMA×CD3 Bispecific Antibody

To evaluate the toxic reaction of AP163 given twice a week by repeated intravenous infusion to cynomolgus monkeys for 2 weeks, and to determine the appropriate dose range and observation index for the subsequent toxicity test. Six cynomolgus monkeys, 3 males and 3 females, were divided into three groups, one male and one female/group, and were given AP163 at 0.1, 0.5 and 2.5 mg/kg respectively (Group 1, 2 or 3). The infusion rate was 30 mL/kg/h and the administration volume was 10 mL/kg. All animals were euthanized on D15 after the end of the 14-day (D14) administration period.

During the experiment, the clinical symptoms, body weight, food intake, body temperature, electrocardiogram, blood pressure, clinical and pathological indicators (blood cell count, coagulation function indicators and blood biochemistry), lymphocyte subsets, cytokines, drug plasma concentration determination and toxicity analysis were monitored periodically. All animals were dissected roughly. Gross anatomical observation showed no obvious abnormality, and no histopathological examination was performed. The results showed that under the experimental conditions, AP163 of 0.1, 0.5 and 2.5 mg/kg was administered twice a week, and repeatedly given to cynomolgus monkeys by intravenous infusion for 2 weeks, and no death or near-death was found in all animals of each administration group, ransient decreases of Neut, CD3-CD20+, TNF-α, IL-2 and IL-6 and Lymph, CD3+, CD3-CD16+/CD56+ were observed after the first administration, maximum tolerated dose (MTD)≥2.5 mg/kg.

Embodiment 7 Pharmacokinetic Test of Anti-BCMA×CD3 Bispecific Antibody

A total of 6 cynomolgus monkeys (3 males and 3 females) were divided into 3 groups, 1 male and 1 female/group, and were given AP163 at 0.1, 0.5 and 2.5 mg/kg respectively. Toxic blood samples (about 1 mL) were collected from the non-administration site of subcutaneous vein of hind limbs of animals to the tubes without anticoagulants, the time points of blood collection in groups 1 to 3 were as follows: before the first and last administration, immediately after the end of administration (±1 min), and 1 h, 3 h, 6 h, 8 h, 24 h, 48 h and 72 h after the start of administration.

Centrifugal tubes (not anticoagulated) shall be stored in ice water bath before use; after blood samples were collected, they were transferred to the centrifuge tube, and then centrifuged at 2~8° C. and 3000×g for 10 min. After separating serum samples, divide them into 2 parts and store them below −70° C. Blood sample collection and centrifugation should be completed within 2 hours.

ELISA method was used to detect and analyze the concentration of AP163 in serum, and non-atrioventricular model (NCA) method of WinNonlin 8.0 software was used to calculate the pharmacokinetic parameters of each group. The results showed that the in vivo half-lives of AP163 in 0.1, 0.5 and 2.5 mg/kg groups were 7.08, 8.95 and 11.42 hours respectively.

TABLE 6 calculation of pharmacokinetic parameters of AP163 after intravenous injection of cynomolgus monkeys

| Dose (mg/kg) | t½ (h) | Tmax (h) | Cmax (µg/mL) | AUClast (h*µg/mL) | AUCINF (h*µg/mL) | Vz (mL/kg) | Cl (mL/h/kg) |
|---|---|---|---|---|---|---|---|
| 0.1 | 7.08 | 0.66 | 2.12 | 20.95 | 21.14 | 48.74 | 4.76 |
| 0.5 | 8.95 | 1 | 12.49 | 120.19 | 120.64 | 60.92 | 4.55 |
| 2.5 | 11.42 | 0.66 | 48.08 | 430.37 | 431.62 | 94.45 | 5.84 |

While preferred embodiments of the present invention have been illustrated and described, it should be understood that various changes can be made by those skilled in the art in light of the teachings herein without departing from the scope of the present invention.

All documents mentioned in the present invention are incorporated by reference in this application as if each document were individually incorporated by reference. In addition, it should be understood that after reading the foregoing teaching contents of the present invention, those skilled in the art can make various modifications or changes to the present invention, and these equivalent forms also fall behind the scope defined by the appended claims of this application.

What is claimed is:

1. A bispecific antibody, which is composed of two identical polypeptide chains bonded covalently to form a tetravalent homodimer,
   wherein each of the polypeptide chains has the amino acid sequence as set forth in SEQ ID NO: 20,
   wherein each of the polypeptide chains consists of an anti-BCMA (B cell maturation antigen) scFv, a linker peptide L2, an anti-CD3 scFv, and an Fc fragment in order,
   wherein VH (heavy chain variable region) and VL (light chain variable region) within the anti-BCMA scFv and the anti-CD3 scFv are connected by a linker sequence respectively, and wherein the amino acid sequence of the linker sequence is amino acids 3-17 of SEQ ID NO: 10,
   wherein the amino acid sequences of the VH and the VL of the anti-BCMA scFv are SEQ ID NO: 7 and SEQ ID NO: 8, respectively,
   wherein the amino acid sequences of the VH and the VL of the anti-CD3 scFv are SEQ ID NO: 17 and SEQ ID NO: 18, respectively,
   wherein the linker peptide L2 consists of a flexible peptide and a rigid peptide,
   wherein the amino acid sequence of the flexible peptide is SEQ ID NO: 29 G2, and
   wherein the amino acid sequence of the rigid peptide is SEQ ID NO: 24.

2. A pharmaceutical composition, comprising the bispecific antibody of claim 1 and a pharmaceutically acceptable excipient and/or carrier and/or diluent.

3. A DNA molecule, encoding the polypeptide chain as set forth in SEQ ID NO: 20.

4. The DNA molecule of claim 3, having the nucleotide sequence as set forth in SEQ ID NO: 21.

5. An expression vector, comprising the DNA molecule of claim 3.

6. An expression vector, comprising the DNA molecule of claim 4.

7. A host cell, which is transformed or transfected with the expression vector of claim 5.

8. A host cell, which is transformed or transfected with the expression vector of claim 6.

9. The host cell of claim 7, wherein the host cell is a prokaryotic cell or a yeast cell or a mammalian cell.

10. The host cell of claim 8, wherein the host cell is a prokaryotic cell or a yeast cell or a mammalian cell.

11. The host cell of claim 7, wherein the host cell is a mammalian cell.

12. The host cell of claim 8, wherein the host cell is a mammalian cell.

13. The host cell of claim 11, wherein the mammalian cell is a CHO cell or a NS0 cell.

14. The host cell of claim 12, wherein the mammalian cell is a CHO cell or a NS0 cell.

15. A method of preparing the bispecific antibody of claim 1, comprising:
   (a) constructing an expression vector comprising a nucleic acid molecule which either comprises the nucleotide sequence as set forth in SEQ ID NO: 21, or encodes the polypeptide chain as set forth in SEQ ID NO: 20, wherein said nucleic acid molecule encodes a polypeptide chain of the bispecific antibody, and wherein two of said polypeptide chain are capable of bonding covalently with each other to form a tetravalent homodimer;
   (b) transfecting said expression vector into a host cell in a culture;
   (c) culturing said host cell under conditions allowing expression and homodimerization of said polypeptide chain to produce the bispecific antibody; and
   (d) separating and purifying the bispecific antibody from the culture.

* * * * *

UNITED STATES PATENT AND TRADEMARK OFFICE
CERTIFICATE OF CORRECTION

PATENT NO. : 12,030,939 B2
APPLICATION NO. : 17/290401
DATED : July 9, 2024
INVENTOR(S) : Qiang Li et al.

Page 1 of 1

It is certified that error appears in the above-identified patent and that said Letters Patent is hereby corrected as shown below:

In the Claims

Column 53, Line 43, Claim 1, replace "SEQ ID NO: 29 G2, and" with --SEQ ID NO: 29, and--.

Signed and Sealed this
Eighth Day of October, 2024

Katherine Kelly Vidal
*Director of the United States Patent and Trademark Office*

SEQUENCE LISTING

<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: HCDR1 of first single chain Fv of bispecific antibody targeting CD3 and BCMA

```
<400> SEQUENCE: 1

Asn Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2 of first single chain Fv of bispecific
      antibody targeting CD3 and BCMA

<400> SEQUENCE: 2

Ala Thr Tyr Arg Gly His Ser Asp Thr Tyr Tyr Asn Gln Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: HCDR3 of first single chain Fv of bispecific
      antibody targeting CD3 and BCMA

<400> SEQUENCE: 3

Gly Ala Ile Tyr Asp Gly Tyr Asp Val Leu Asp Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: LCDR1 of first single chain Fv of bispecific
      antibody targeting CD3 and BCMA

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2 of first single chain Fv of bispecific
      antibody targeting CD3 and BCMA

<400> SEQUENCE: 5

Tyr Thr Ser Asn Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3 of first single chain Fv of bispecific
      antibody targeting CD3 and BCMA

<400> SEQUENCE: 6

Gln Gln Tyr Arg Lys Leu Pro Trp Thr
1               5

<210> SEQ ID NO 7
```

```
<211> LENGTH: 121
<212> TYPE: PRT
<213> ORGANISM: Artificial Sequence
<220> FEATURE:
<223> OTHER INFORMATION: VH domain of first single chain Fv of
      bispecific antibody targeting CD3 and BCMA

<400> SEQUENCE: 7
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120

```
<210> SEQ ID NO 8
<211> LENGTH: 107
<212> TYPE: PRT
<213> ORGANISM: Artificial Sequence
<220> FEATURE:
<223> OTHER INFORMATION: VL domain of first single chain Fv of
      bispecific antibody targeting CD3 and BCMA

<400> SEQUENCE: 8
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys
            100                 105

```
<210> SEQ ID NO 9
<211> LENGTH: 28
<212> TYPE: PRT
<213> ORGANISM: Artificial Sequence
<220> FEATURE:
<223> OTHER INFORMATION: full-length sequence consisting of amino acids
      at positions 118 to 145 derived from the carboxyl terminal of
      natural human chorionic gonadotropin beta subunit

<400> SEQUENCE: 9
```

Ser Ser Ser Ser Lys Ala Pro Pro Pro Ser Leu Pro Ser Pro Ser Arg
1               5                   10                  15

```
Leu Pro Gly Pro Ser Asp Thr Pro Ile Leu Pro Gln
            20                  25

<210> SEQ ID NO 10
<211> LENGTH: 27
<212> TYPE: PRT
<213> ORGANISM: Artificial Sequence
<220> FEATURE:
<223> OTHER INFORMATION: linker peptide L2

<400> SEQUENCE: 10

Gly Gly Gly Gly Gly Gly Ser Gly Gly Gly Gly Ser Gly Gly Gly Gly
1               5                   10                  15

Ser Ser Ser Ser Ser Lys Ala Pro Pro Pro Ser
            20                  25

<210> SEQ ID NO 11
<211> LENGTH: 5
<212> TYPE: PRT
<213> ORGANISM: Artificial Sequence
<220> FEATURE:
<223> OTHER INFORMATION: HCDR1 of second single chain Fv of bispecific
      antibody targeting CD3 and BCMA

<400> SEQUENCE: 11

Thr Tyr Ala Met Asn
1               5

<210> SEQ ID NO 12
<211> LENGTH: 19
<212> TYPE: PRT
<213> ORGANISM: Artificial Sequence
<220> FEATURE:
<223> OTHER INFORMATION: HCDR2 of second single chain Fv of bispecific
      antibody targeting CD3 and BCMA

<400> SEQUENCE: 12

Arg Ile Arg Ser Lys Tyr Asn Asn Tyr Ala Thr Tyr Tyr Ala Asp Ser
1               5                   10                  15

Val Lys Asp

<210> SEQ ID NO 13
<211> LENGTH: 14
<212> TYPE: PRT
<213> ORGANISM: Artificial Sequence
<220> FEATURE:
<223> OTHER INFORMATION: HCDR3 of second single chain Fv of bispecific
      antibody targeting CD3 and BCMA

<400> SEQUENCE: 13

His Gly Asn Phe Gly Asn Ser Tyr Val Ser Trp Phe Ala Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: LCDR1 of second single chain Fv of bispecific
      antibody targeting CD3 and BCMA

<400> SEQUENCE: 14

Arg Ser Ser Thr Gly Ala Val Thr Thr Ser Asn Tyr Ala Asn
1               5                   10
```

```
<210> SEQ ID NO 15
<211> LENGTH: 7
<212> TYPE: PRT
<213> ORGANISM: Artificial Sequence
<220> FEATURE:
<223> OTHER INFORMATION: LCDR2 of second single chain Fv of bispecific
      antibody targeting CD3 and BCMA

<400> SEQUENCE: 15

Gly Thr Asn Lys Arg Ala Pro
1               5

<210> SEQ ID NO 16
<211> LENGTH: 9
<212> TYPE: PRT
<213> ORGANISM: Artificial Sequence
<220> FEATURE:
<223> OTHER INFORMATION: LCDR3 of second single chain Fv of bispecific
      antibody targeting CD3 and BCMA

<400> SEQUENCE: 16

Ala Leu Trp Tyr Ser Asn Leu Trp Val
1               5

<210> SEQ ID NO 17
<211> LENGTH: 125
<212> TYPE: PRT
<213> ORGANISM: Artificial Sequence
<220> FEATURE:
<223> OTHER INFORMATION: VH domain of second single chain Fv of
      bispecific antibody targeting CD3 and BCMA

<400> SEQUENCE: 17

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 18
<211> LENGTH: 109
<212> TYPE: PRT
<213> ORGANISM: Artificial Sequence
<220> FEATURE:
<223> OTHER INFORMATION: VL domain of second single chain Fv of
      bispecific antibody targeting CD3 and BCMA

<400> SEQUENCE: 18

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                    85                  90                  95

Leu Trp Val Phe Gly Gly Gly Thr Lys Leu Thr Val Leu
                100                 105

<210> SEQ ID NO 19
<211> LENGTH: 226
<212> TYPE: PRT
<213> ORGANISM: Artificial Sequence
<220> FEATURE:
<223> OTHER INFORMATION: Fc fragment

<400> SEQUENCE: 19

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Gln Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly
225

<210> SEQ ID NO 20
<211> LENGTH: 764
<212> TYPE: PRT
<213> ORGANISM: Artificial Sequence
<220> FEATURE:
<223> OTHER INFORMATION: amino acid sequence of bispecific antibody,
      which binds to human BCMA and CD3

<400> SEQUENCE: 20

```
Met Arg Ser Leu Gly Ala Leu Leu Leu Leu Ser Ala Cys Leu Ala
1               5                   10                  15

Val Ser Ala Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
            35                  40                  45

Ser Asn Tyr Trp Met His Trp Val Arg Gln Ala Pro Gly Gln Gly Leu
50                  55                  60

Glu Trp Met Gly Ala Thr Tyr Arg Gly His Ser Asp Thr Tyr Tyr Asn
65              70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
                100                 105                 110

Tyr Tyr Cys Ala Arg Gly Ala Ile Tyr Asp Gly Tyr Asp Val Leu Asp
            115                 120                 125

Asn Trp Gly Gln Gly Thr Leu Val Thr Val Ser Ser Gly Gly Gly Gly
130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Ser Ala Ser Gln Asp Ile Ser Asn Tyr Leu Asn Trp Tyr Gln
            180                 185                 190

Gln Lys Pro Gly Lys Ala Pro Lys Leu Leu Ile Tyr Tyr Thr Ser Asn
            195                 200                 205

Leu His Ser Gly Val Pro Ser Arg Phe Ser Gly Ser Gly Ser Gly Thr
210                 215                 220

Asp Phe Thr Leu Thr Ile Ser Ser Leu Gln Pro Glu Asp Phe Ala Thr
225                 230                 235                 240

Tyr Tyr Cys Gln Gln Tyr Arg Lys Leu Pro Trp Thr Phe Gly Gln Gly
            245                 250                 255

Thr Lys Leu Glu Ile Lys Gly Gly Gly Gly Ser Gly Gly Gly
            260                 265                 270

Gly Ser Gly Gly Gly Gly Ser Ser Ser Lys Ala Pro Pro
            275                 280                 285

Ser Glu Val Gln Leu Leu Glu Ser Gly Gly Leu Val Gln Pro Gly
            290                 295                 300

Gly Ser Leu Lys Leu Ser Cys Ala Ala Ser Gly Phe Thr Phe Asn Thr
305                 310                 315                 320

Tyr Ala Met Asn Trp Val Arg Gln Ala Pro Gly Lys Gly Leu Glu Trp
                325                 330                 335

Val Ala Arg Ile Arg Ser Lys Tyr Asn Asn Tyr Ala Thr Tyr Tyr Ala
                340                 345                 350

Asp Ser Val Lys Asp Arg Phe Thr Ile Ser Arg Asp Asp Ser Lys Asn
            355                 360                 365

Thr Ala Tyr Leu Gln Met Asn Asn Leu Lys Thr Glu Asp Thr Ala Val
            370                 375                 380

Tyr Tyr Cys Val Arg His Gly Asn Phe Gly Asn Ser Tyr Val Ser Trp
385                 390                 395                 400

Phe Ala Tyr Trp Gly Gln Gly Thr Leu Val Thr Val Ser Ser Gly Gly
                405                 410                 415
```

-continued

Gly Gly Ser Gly Gly Gly Ser Gly Gly Gly Ser Glu Leu Val
            420             425             430

Val Thr Gln Glu Pro Ser Leu Thr Val Ser Pro Gly Gly Thr Val Thr
            435                 440                 445

Leu Thr Cys Arg Ser Ser Thr Gly Ala Val Thr Thr Ser Asn Tyr Ala
450                 455                 460

Asn Trp Val Gln Gln Lys Pro Gly Gln Ala Pro Arg Gly Leu Ile Gly
465                 470                 475                 480

Gly Thr Asn Lys Arg Ala Pro Gly Thr Pro Ala Arg Phe Ser Gly Ser
            485                 490                 495

Leu Leu Gly Gly Lys Ala Ala Leu Thr Leu Ser Gly Val Gln Pro Glu
            500                 505                 510

Asp Glu Ala Glu Tyr Tyr Cys Ala Leu Trp Tyr Ser Asn Leu Trp Val
            515                 520                 525

Phe Gly Gly Gly Thr Lys Leu Thr Val Leu Asp Lys Thr His Thr Cys
            530                 535                 540

Pro Pro Cys Pro Ala Pro Glu Ala Ala Gly Gly Pro Ser Val Phe Leu
545                 550                 555                 560

Phe Pro Pro Lys Pro Lys Asp Gln Leu Met Ile Ser Arg Thr Pro Glu
                565                 570                 575

Val Thr Cys Val Val Val Asp Val Ser His Glu Asp Pro Glu Val Lys
            580                 585                 590

Phe Asn Trp Tyr Val Asp Gly Val Glu Val His Asn Ala Lys Thr Lys
            595                 600                 605

Pro Arg Glu Glu Gln Tyr Ala Ser Thr Tyr Arg Val Val Ser Val Leu
            610                 615                 620

Thr Val Leu His Gln Asp Trp Leu Asn Gly Lys Glu Tyr Lys Cys Lys
625                 630                 635                 640

Val Ser Asn Lys Ala Leu Pro Ala Ser Ile Glu Lys Thr Ile Ser Lys
                645                 650                 655

Ala Lys Gly Gln Pro Arg Glu Pro Gln Val Tyr Thr Leu Pro Pro Ser
            660                 665                 670

Arg Asp Glu Leu Thr Lys Asn Gln Val Ser Leu Thr Cys Leu Val Lys
            675                 680                 685

Gly Phe Tyr Pro Ser Asp Ile Ala Val Glu Trp Glu Ser Asn Gly Gln
            690                 695                 700

Pro Glu Asn Asn Tyr Lys Thr Thr Pro Pro Val Leu Asp Ser Asp Gly
705                 710                 715                 720

Ser Phe Phe Leu Tyr Ser Lys Leu Thr Val Asp Lys Ser Arg Trp Gln
                725                 730                 735

Gln Gly Asn Val Phe Ser Cys Ser Val Leu His Glu Ala Leu His Asn
            740                 745                 750

His Tyr Thr Gln Lys Ser Leu Ser Leu Ser Pro Gly
            755                 760

<210> SEQ ID NO 21
<211> LENGTH: 2313
<212> TYPE: DNA
<213> ORGANISM: Artificial Sequence
<220> FEATURE:
<223> OTHER INFORMATION: DNA sequence of bispecific antibody, which
      binds to human BCMA and CD3

<400> SEQUENCE: 21
actagtcgcc accatgagga gcctcggggc cctgctcttg ctgctgagcg cctgcctggc    60

```
ggtgagcgct caggtgcagc tggtgcagtc tggcgctgag gtgaagaagc ccggcagctc    120
tgtgaaggtg tcttgtaagg cctccggcgg caccttctcc aactattgga tgcattgggt    180
gcgccaggct cctggccagg gcctggagtg gatgggagct acctacaggg acactccga     240 cacatattac aatcagaagt ttaagggcag ggtgacaatc accgctgata agtctacatc    300
caccgcctac atggagctgt ccagcctgcg gagcgaggac accgccgtgt attactgcgc    360
cagaggcgct atctacgatg ctatgacgt gctggataac tggggccagg gcacactggt     420
gaccgtgtct tccggaggag gaggatctgg aggaggaggc tccggaggag gaggaagcga    480
tatccagatg acccagagcc caagctctct gtccgcctct gtgggcgata gggtgacaat    540
cacctgttcc gccagccagg acatctctaa ctacctgaat tggtatcagc agaagcccgg    600
caaggctcct aagctgctga tctattacac cagcaatctg cattctggag tgccttcccg    660
cttctctggc tccggaagcg gaacagactt tacactgacc atctccagcc tgcagccaga    720
ggatttcgcc acttactact gccagcagta caggaagctg ccctggacct ttggccaggg    780
taccaagctg gagatcaagg gtggcggcgg tggaggatcc ggcggtggag gtagcggcgg    840
aggcggtagc tccagctcta gtaaagctcc ccctccttcc gaggtgcagc tgctggagtc    900
cggaggagga ctggtgcagc caggaggctc cctgaagctg agctgtgctg cctctggctt    960
taccttcaac acatatgcca tgaattgggt gcggcaggct ccaggcaagg gactggagtg    1020
ggtggctagg atcaggtcta agtacaacaa ttatgccacc tactatgctg attccgtgaa    1080
ggacaggttc accatctccc gcgacgatag caagaacaca gcctacctgc agatgaacaa    1140
tctgaagacc gaggataccg ccgtgtacta ctgcgtgaga catggcaact tggcaatag      1200 ctacgtgtcc tggttcgctt actggggaca gggcaccctg gtcacagtga gctctggagg    1260
aggaggatct ggaggaggag gctccggagg aggaggaagc gagctggtgg tgacccagga    1320
gccatctctg acagtgtccc ccggcggcac agtgaccctg acatgtagat ccagcaccgg    1380
cgccgtgacc acatccaact acgctaattg ggtgcagcag aagccaggac aggctccaag    1440
gggactgatc ggaggaacca acaagagggc tcctggaaca ccagctcggt ttagcggatc    1500
tctgctggga ggcaaggctg ccctgaccct gtccggagtg cagccagagg atgaggccga    1560
gtattattgc gctctgtggt atagcaatct gtgggtgttc ggaggaggaa ccaagctgac    1620
agtgctggac aagacccata catgcccacc atgccctgcc cctgaagccg ccggaggacc    1680
ttccgtgttc ctgttccctc ccaagccaaa agatcagctg atgatctcta gaaccccccga   1740 agtcacctgc gtggtcgtcg acgtgtccca tgaggaccct gaagtcaagt tcaactggta    1800
cgtggacggt gtcgaagtcc acaacgccaa gaccaagcct agggaggagc agtatgccag    1860
cacataccgg gtggtgtctg tgctgaccgt gctgcatcag gattggctga atggcaagga    1920
atataaatgt aaggtgagca ataaggctct gccggctagc attgaaaaaa ccatttccaa    1980
ggctaagggc cagcccaggg agcctcaggt ctacaccctg cctccatcta gagatgaact    2040
gaccaaaaac caggtgagcc tgacttgcct ggtcaaaggc ttctacccca gcgacattgc    2100
cgtggagtgg gagtctaatg gccagccga aaataactac aaaactaccc ctcctgtgct     2160
ggactctgat ggctccttct ttctgtactc taaactgacc gtggacaagt ctcgctggca    2220
gcagggtaac gtgttttctt gctccgtgct gcacgaggct ctgcataacc attcaccca     2280 gaagagcctg tctctgtccc caggatagaa ttc                                 2313
```

<210> SEQ ID NO 22

```
<211> LENGTH: 5
<212> TYPE: PRT
<213> ORGANISM: Artificial Sequence
<220> FEATURE:
<223> OTHER INFORMATION: linker sequence

<400> SEQUENCE: 22

Gly Gly Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: linker sequence
<220> FEATURE:
<221> NAME/KEY: misc_feature
<222> LOCATION: (5)..(5)
<223> OTHER INFORMATION: Xaa = Ser or Ala

<400> SEQUENCE: 23

Gly Gly Gly Gly Xaa
1               5

<210> SEQ ID NO 24
<211> LENGTH: 10
<212> TYPE: PRT
<213> ORGANISM: Artificial Sequence
<220> FEATURE:
<223> OTHER INFORMATION: CPT1

<400> SEQUENCE: 24

Ser Ser Ser Ser Lys Ala Pro Pro Pro Ser
1               5                   10

<210> SEQ ID NO 25
<211> LENGTH: 14
<212> TYPE: PRT
<213> ORGANISM: Artificial Sequence
<220> FEATURE:
<223> OTHER INFORMATION: CPT2

<400> SEQUENCE: 25

Ser Arg Leu Pro Gly Pro Ser Asp Thr Pro Ile Leu Pro Gln
1               5                   10

<210> SEQ ID NO 26
<211> LENGTH: 16
<212> TYPE: PRT
<213> ORGANISM: Artificial Sequence
<220> FEATURE:
<223> OTHER INFORMATION: CPT3

<400> SEQUENCE: 26

Ser Ser Ser Ser Lys Ala Pro Pro Pro Ser Leu Pro Ser Pro Ser Arg
1               5                   10                  15

<210> SEQ ID NO 27
<211> LENGTH: 28
<212> TYPE: PRT
<213> ORGANISM: Artificial Sequence
<220> FEATURE:
<223> OTHER INFORMATION: CPT4

<400> SEQUENCE: 27

Ser Ser Ser Ser Lys Ala Pro Pro Pro Ser Leu Pro Ser Pro Ser Arg
1               5                   10                  15
```

```
Leu Pro Gly Pro Ser Asp Thr Pro Ile Leu Pro Gln
            20                  25

<210> SEQ ID NO 28
<211> LENGTH: 5
<212> TYPE: PRT
<213> ORGANISM: Artificial Sequence
<220> FEATURE:
<223> OTHER INFORMATION: linker sequence

<400> SEQUENCE: 28

Gly Gly Gly Gly Ala
1               5
```